(12) United States Patent
Jeong et al.

(10) Patent No.: US 9,310,326 B2
(45) Date of Patent: Apr. 12, 2016

(54) DEVICE FOR DETERMINING A MONOMER MOLECULE SEQUENCE OF A POLYMER COMPRISING DIFFERENT ELECTRODES AND USE THEREOF

(71) Applicant: Samsung Electronics Co., Ltd., Suwon-si, Gyeonggi-do (KR)

(72) Inventors: Heejeong Jeong, Seoul (KR); Jeo-young Shim, Yongin-si (KR); Kun-sun Eom, Seoul (KR); Dong-ho Lee, Seongnam-si (KR); Tae-han Jeon, Hwaseong-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 490 days.

(21) Appl. No.: 13/918,317

(22) Filed: Jun. 14, 2013

(65) Prior Publication Data
US 2013/0334047 A1   Dec. 19, 2013

(30) Foreign Application Priority Data

Jun. 14, 2012 (KR) .................. 10-2012-0063865
Aug. 27, 2012 (KR) .................. 10-2012-0093889

(51) Int. Cl.
*G01N 27/327* (2006.01)
*G01N 27/447* (2006.01)
*G01N 27/00* (2006.01)
*G01N 33/487* (2006.01)

(52) U.S. Cl.
CPC .......... *G01N 27/00* (2013.01); *G01N 33/48721* (2013.01); *G01N 27/4473* (2013.01)

(58) Field of Classification Search
CPC ................. G01N 33/48721; G01N 27/4473
See application file for complete search history.

(56) References Cited

U.S. PATENT DOCUMENTS

| | | | |
|---|---|---|---|
| 6,905,586 B2 | 6/2005 | Lee et al. | |
| 7,556,922 B2 | 7/2009 | Block et al. | |
| 7,876,108 B2 | 1/2011 | Abassi et al. | |
| 2005/0130296 A1 | 6/2005 | Pisharody et al. | |
| 2005/0202444 A1 | 9/2005 | Zhu | |
| 2007/0238112 A1* | 10/2007 | Sohn ................. | B01L 3/502761 435/6.19 |
| 2008/0149479 A1 | 6/2008 | Olofsson et al. | |
| 2012/0193237 A1* | 8/2012 | Afzali-Ardakani .... | B82Y 15/00 204/627 |

OTHER PUBLICATIONS

Prasongkit et al., "Transverse Conductance of DNA Nucleotides in a Graphene Nanogap from First Principles," *Nano Letters*, 11: 1941-1945 (2011).
Pedone et al., "Fabrication and electrical characterization of a pore-cavity-pore device," *Journal of Physics: Condensed Matter*, 22: 1-8 (2010).
Krems et al., "Effect of Noise on DNA Sequencing via Transverse Electronic Transport," *Biophysical Journal*, 97: 1990-1996 (2009).
Tsutsui et al., "Single-molecule sensing electrode embedded in-plane nanopore," *Scientific Reports*, 1(46): 1-6 (2011).

* cited by examiner

*Primary Examiner* — Alexander Noguerola
(74) *Attorney, Agent, or Firm* — Leydig, Voit & Mayer, Ltd.

(57) ABSTRACT

Provided is a device for determining a monomer molecule sequence of a polymer including different electrodes, and a method of efficiently determining a monomer molecule sequence of a polymer.

22 Claims, 30 Drawing Sheets

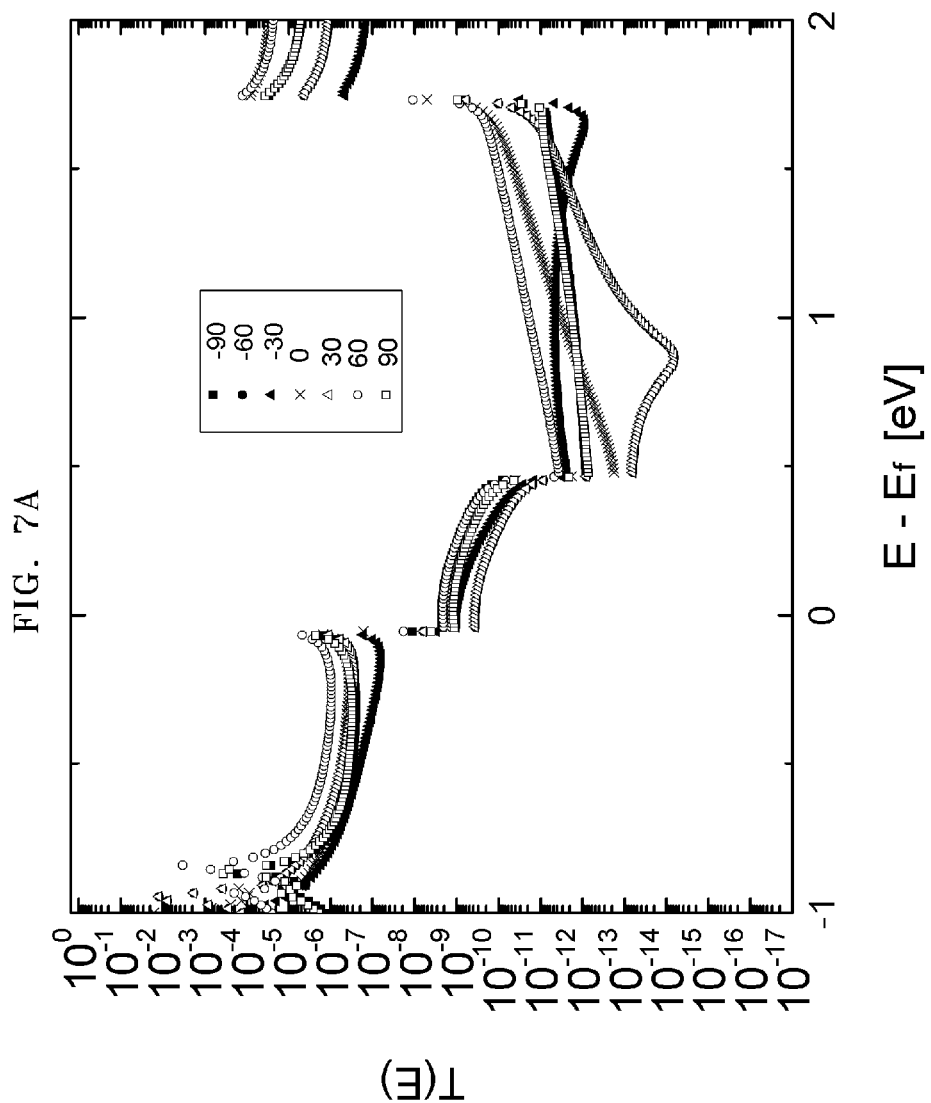

DEVICE FOR DETERMINING A MONOMER MOLECULE SEQUENCE OF A POLYMER COMPRISING DIFFERENT ELECTRODES AND USE THEREOF

CROSS-REFERENCE TO RELATED APPLICATIONS

This application claims the benefit of Korean Patent Application No. 10-2012-0063865, filed on Jun. 14, 2012 and Korean Patent Application No. 10-2012-0093889, filed on Aug. 27, 2012, in the Korean Intellectual Property Office, the disclosure of which is incorporated herein in its entirety by reference.

BACKGROUND

1. Field

The present disclosure relates to devices for determining a monomer molecule sequence of a polymer including different electrodes, and methods of efficiently determining a monomer molecule sequence of a polymer.

2. Description of the Related Art

Research into determining primary sequences of monomers of biopolymers has been conducted. Identification of sequences of monomers is intrinsic for identifying functions of biopolymers. It is becoming increasingly important to quickly, reliably, and inexpensively identify features of polymers, particularly, nucleic acids. Typical sequencing of nucleic acids depends on chemical reactions generating DNA fragments cleaved at specific bases and having various lengths and enzymatic reactions generating DNA fragments having various lengths and terminated at a specific base.

Recently, research into sequencing of molecules of nucleic acids by the development of natural or synthetic nanopores has been conducted. In the nanopore sequencing, single-stranded DNAs pass through nanopores in an appropriate solution, and physical changes of individual nucleotides or environment of nucleotides are sensed. For example, a membrane having nanopores separates two chambers in a solution, and a voltage is applied therebetween. Ionic current in the solution between the two chambers flowing through the nanopores is used to monitor existence of DNA in the nanopores. If a single-stranded DNA is within the nanopores, the nanopores are partially blocked to reduce the ionic current between the two chambers.

There is a need to identify polymers such as biomolecules and/or determine a sequence thereof in the art.

SUMMARY

Provided are devices for efficiently determining a monomer molecule sequence of a polymer.

Provided are methods of efficiently determining a monomer molecule sequence of a polymer.

Additional aspects will be set forth in part in the description which follows and, in part, will be apparent from the description, or may be learned by practice of the presented embodiments.

According to an aspect of the present invention, a device for determining a monomer molecule sequence of a polymer includes: a pair of first electrodes that are formed of a first material and separated from each other by a gap; a pair of second electrodes that are separated from each other by a gap and formed of a material having electrical characteristics different from the electrical characteristics of the material of the first electrodes; a pair of insulating materials between the pair of first electrodes and the pair of second electrodes, wherein the pair of insulating materials are separated from each other by a gap; wherein the gap separating the pair of first electrodes, the gap separating the pair of insulating materials, and the gap separating the pair of second electrodes are stacked in alignment to form a path through which the polymer can move; electrical signal detectors respectively connected to the pair of first electrodes and the pair of second electrodes; a polymer positioning unit for disposing the polymer in the path; and a polymer moving unit for rotating or left-right shifting the polymer disposed in the path.

The path may have a cross-sectional length to allow the polymer to pass therethrough. The polymer may be nucleic acid or protein. The nucleic acid may be DNA, RNA, or chimeric molecules thereof. The monomer molecule of the polymer is a basic building block constituting the polymer. The monomer molecule of nucleic acid may be nucleotide or base, and the monomer molecule of protein may be amino acid. The path may have a cross-sectional length to allow a single molecule of the polymer to pass therethrough. One end or both ends of the polymer may be connected to a nanoparticle or microparticle. For example, the cross-sectional length of the path may be about 10 nm or less, for example, in a range of about 1 nm to about 10 nm, about 1 to about 8 nm, about 1 to about 6 nm, about 2 to about 10 nm, about 3 to about 10 nm, about 1 nm to about 5 nm, about 1 to about 4 nm, about 1 to about 3 nm, about 2 to about 5 nm, or about 3 to about 5 nm. The path may have a circular or polygonal cross-section. If the path has a circular cross-section, the cross-sectional length refers to a diameter. The path may have a shape partially or entirely open in the transverse direction across the path or may have a pore or channel shape that is partially or entirely closed, for example, a nanopore or nanochannel shape. The nanoparticle or microparticle may have various shapes such as bead, sphere, or polyprism shape. The nanoparticle or microparticle may include a magnetic particle, for example, metallic material. The nanoparticle or microparticle may have a cross-sectional length unsuitable for passing through the path.

The first electrode pair and the second electrode pair may have different electrical characteristics (e.g., one or more different electrical properties, such as conductivity, Fermi-level, density of states, resistivity, dielectric constant, etc.). Thus, if the polymer is positioned in the path or passes through the path, the first electrode pair and the second electrode pair may generate different electrical signals according to the monomer molecule of the polymer. The first electrode pair and the second electrode pair may respectively generate electrical signals capable of distinguishing all monomer molecules of the polymer. In addition, although the first electrode pair and the second electrode pair do not individually generate electrical signals capable of distinguishing all monomer molecules of the polymer, a monomer molecule that is not distinguished by the electrical signal of the first electrode pair may be distinguished by the electrical signal of the second electrode pair. That is, all monomer molecules of the polymer may be distinguished from each other by combining electrical signals from the pair of first electrodes and the pair of second electrodes. The individual electrodes constituting the first or second pair of electrodes may be formed of different materials. In other words, a pair of electrodes may comprise one electrode of a first material and another electrode of a second material, in which case the electrode pair comprises a combination of electrode materials. The first electrode pair and the second electrode pair may have different electrical characteristics if the first electrode and the second electrode pairs are formed of different materials or combinations of different electrodes. For example, if the first electrode pair is formed of a combination of graphene electrode-graphene electrode or graphene electrode-gold electrode, and the second electrode pair is formed of a combination of graphene electrode-gold electrode or gold electrode-gold electrode, the first electrode pair and the second electrode pair may have different electrical characteristics due to the different combinations of electrodes in each pair, although both pairs of electrodes include a graphene electrode or a gold electrode. The first electrode pair and the second electrode pair may not define all of the internal walls of the path, but are instead separated from each other on the internal walls of the path.

The first electrode pair may include a carbonaceous electrode, metal electrode, or any combination thereof, and the second electrode pair may include a carbonaceous electrode, a metal electrode, or any combination thereof. The carbonaceous electrode may be a graphene electrode or carbon nanotube (CNT) electrode. Edges of the coarbonaceous electrode may be modified. For example, the edges may be hydrogen-terminated, for example, H-type graphene electrode, or an oxidized terminal, e.g., hydroxyl-(OH type) terminated, lactone-terminted, ketone-terminated, ether-terminated, or any combination thereof. The pair of first electrodes and the pair of second electrodes may be different from each other by the combination of a H-type carbonaceous electrode and an oxidized carbonaceous electrode (e.g., OH-type). The metal electrode may be selected from the group consisting of gold, silver, platinum, copper, lead, chromium, titanium, nickel, zinc, iron, tin, or any combination thereof. According to a particular embodiment, the pair of first electrodes may include a graphene electrode or gold electrode, and the pair of second electrodes may include a gold electrode or graphene electrode.

The insulating materials may include an organic insulating material, an inorganic insulating material, and any combination thereof. The organic insulating material may be selected from the group consisting of an elastomer, a polymeric material, a cellulose material, and a lipidic material. The inorganic insulating material may be selected from the group consisting of glass, mineral oxide (e.g., $SiO_2$), and nitride (e.g., silicon nitride).

A stack of the first electrodes, the insulating materials, and the second electrodes may have a path penetrating the stack in the transverse direction across the stack (i.e., in a direction substantially perpendicular to the direction in which the first electrodes, insulating materials and second electrodes are stacked). The stack has a first side comprising a first side (end or opening) of the path into which the polymer is introduced and a second side comprising a second side (end or opening) of the path from which the polymer is discharged. The device is disposed to be able to move in the transverse direction across the path with respect to at least one of the first and second sides, and may further include a substrate capable of immobilizing the polymer. The term "substrate capable of immobilizing the polymer" refers to a substrate having a specific or non-specific moiety capable of binding to the polymer on the surface thereof. For example, the polymer may be a nucleic acid having a hydroxyl group or a phosphate group at an at least one of the 3'-end and 5'-end, and the substrate may have a moiety that may bind to at least one of the hydroxyl group and phosphate group on the surface. In addition, for example, the polymer may be a nucleic acid having a thiol group at an at least one of the 3'-end and 5'-end, and the substrate may be a gold electrode, the surface of which may be bound to the thiol group. The term "disposed to be able to move" includes disposed to be able to slide.

In the device, the electrical signal detector may detect current, voltage, resistance, impedance, or any combination thereof. For example, the electrical signal detector is to detect a tunneling current that is generated when the polymer is held in the path or passes through the path.

In the device, the unit for disposing the polymer in the path refers to a unit capable of transporting the polymer to the path. For example, the unit may be an electric field-providing unit, a mechanical pressure-providing unit, an optical tweezer, a magnetic tweezer, or any combination thereof. The electric field-providing unit may include, for example, a pair of electrodes respectively disposed to face the first and second sides of the path and power sources respectively connected thereto. The mechanical pressure-providing unit may include, for example, a pump disposed to be able to respectively provide a pressure to the first and second sides of the path. In addition, the optical tweezer, the magnetic tweezer, or any combination thereof may be disposed to face at least one of the first and second sides of the path.

The unit for disposing the polymer in the path may be disposed at one side of the path on the substrate to face the other side of the path.

In the device, the unit for rotating or left-right shifting the polymer disposed in the path may be an optical tweezer, a magnetic tweezer, or any combination thereof. The unit may be disposed to face at least one of the first and second sides of the path. The unit for rotating or left-right shifting the polymer may be the same or different from the unit for disposing the polymer in the path.

The device may further include a signal processor that is electrically connected to the electrical signal detector and includes a storage medium storing a computer readable program that determines a monomer sequence of a polymer by using a method including: setting a first threshold value of an intensity of a signal received from the first electrode according to a monomer molecule of a polymer and identifying the type of the monomer based on a signal having an intensity higher than the first threshold value; and setting a second threshold value of an intensity of a signal received from the second electrode according to a monomer molecule of a polymer and identifying the type of the monomer based on a signal having an intensity higher than the second threshold value. The signal processor may be a computer including a microprocessor. The signal may include an average of signals with respect to a travel angle or distance according to the rotation or left-right shift of the polymer. The rotation or left-right shift may be performed while holding the polymer in the path. The holding of the polymer in the path may be performed by immobilizing one end of the polymer on the surface of the substrate and immobilizing the other end of the polymer on the microparticle by applying an optical or magnetic force thereto using an optical or magnetic tweezer.

According to a particular embodiment, the pair of first electrodes of the device may include a graphene electrode, and the pair of second electrodes thereof may include a gold electrode. The polymer may be DNA, and the device may further include a signal processor that includes a storage medium storing a computer readable program that determines a monomer sequence of a polymer by using a method including: setting a first threshold value of an intensity of a signal received from the pair of first electrodes according to a monomer molecule of a polymer as 1 pA; identifying monomer molecules corresponding to the highest value (first value, e.g., G) and the second highest value (second value, e.g., T) among signals having an intensity higher than the first threshold value; setting a second threshold value of an intensity of a signal received from the pair of second electrodes according to a monomer molecule of a polymer as 1 pA; and identifying the type of monomer molecule as A from a signal having an intensity higher than the second threshold value.

The device may be a microfluidic device in which an inlet and an outlet are connected to each other to allow fluid flow therebetween via a microchannel. In addition, the device may include a first container that contacts one side of the path in the transverse direction and contains polymers disposed in the path and a second container that contacts the other side of the path opposite to the one side of the path in the transverse direction and contains polymers discharged from the path. The stack may constitute a portion of at least one of the first and second containers.

According to another aspect of the present invention, a method of determining a monomer molecule sequence of a polymer includes: disposing monomer molecules of a polymer in the path of the device; detecting electrical signals respectively from the pair of first electrodes and the pair of second electrodes; setting a first threshold value of an intensity of a signal received from the pair of first electrodes according to a monomer molecule of a polymer; identifying the type of the monomer molecule from a signal having an intensity higher than the first threshold value; setting a second threshold value of an intensity of a signal received from the pair of second electrodes according to a monomer molecule of a polymer; identifying the type of the monomer from a signal having an intensity higher than the second threshold value; and determining the monomer molecule sequence of the polymer by combining the type of the monomer molecules identified by using the signal from the pair of first electrodes and the type of the monomer molecules identified by using the signal from the pair of second electrodes.

The method includes forming the path by using a pair of first electrodes that are formed of a first material and separated from each other by a gap; a pair of second electrodes that are separated from each other by a gap and formed of a material having electrical characteristics different from the electrical characteristics of the material of the pair of first electrodes; a pair of insulating materials between the pair of first electrodes and the pair of second electrodes, wherein the pair of insulating materials are separated from each other by a gap, wherein the gap separating the pair of first electrodes, the gap separating the pair of insulating materials, and the gap separating the pair of second electrodes are stacked in alignment to form a path through which the polymer can move, as an operation of disposing the monomer molecules of the polymer in the path.

The pair of first electrodes, the pair of second electrodes, the pair of insulating materials, the stack thereof, and the polymer are as described above. In addition, the stack may be contained in the device.

The disposing of the polymer may be performed by electrophoresis by applying a voltage in the transverse direction across the path, for example, by applying a (−) voltage to the first side of the path and applying a (+) voltage to the second side of the path. In addition, the polymer may be disposed in the path by applying a mechanical pressure in the transverse direction across the path, for example, by applying a positive pressure to the first side of the path and applying a negative pressure to the second side of the path. The pressure may be applied by using a pump or the like. In addition, the polymer may be directly disposed in the path by using an optical tweezer or magnetic tweezer.

The disposing of the polymer may include holding the polymer in the path or passing the polymer through the path. The holding of the polymer in the path may be conducted by immobilizing one end of the polymer on the surface of the substrate, immobilizing the other end of the polymer on the microparticle, and applying an optical or magnetic force to the microparticle using an optical or magnetic tweezer. Disposing multiple polymers in the path may be performed by disposing one polymer at a time. The polymer may be DNA, RNA, or any combination thereof.

The holding of the polymer may be performed by holding the polymer at a predetermined position of the path by using the optical tweezer or magnetic tweezer.

According to the method, the polymer includes a nanoparticle or microparticle immobilized on at least one of a first end or second end of the polymer allowing the polymer to be moved by an optical tweezer or magnetic tweezer. The nanoparticle or microparticle may have various shapes such as a bead, sphere, or polyprism shape. The nanoparticle or microparticle may be a magnetic particle. The nanoparticle or microparticle may have a cross-sectional length unsuitable for passing through the path.

The path includes a first end to which the polymer is input and a second end from which the polymer is discharged, and the method may further include immobilizing the polymer on a substrate movable with respect to the first end and the second end in the longitudinal direction along the path. The immobilization may be performed before or after the holding or simultaneously with the holding.

The method includes detecting electrical signals respectively from the pair of first electrodes and the pair of second electrodes. The electrical signal to be detected may be current, voltage, resistance, impedance, or any combination thereof. For example, the electrical signal to be detected may be a tunneling current that is generated while holding the polymer in the path or passing the polymer through the path.

In the method, the detecting of the electrical signals may include detecting a signal according to a travel angle, distance while rotating, or left-right shifting the polymer, and calculating an average of the detected signals according to the travel angle or distance. The rotation or left-right shift may be performed by using an optical tweezer or magnetic tweezer. The rotation or left-right shift may also be performed by applying an optical or magnetic force to the microparticle bound to one end or both ends of the polymer. In this regard, one end or both ends of the polymer may be immobilized on a substrate aligned to be able to move in the transverse direction across the path. A standard position of the polymer before the rotation or left-right shift may be determined by the immobilization.

The method includes setting a first threshold value of an intensity of a signal received from the pair of first electrodes according to a monomer molecule of a polymer and identifying the type of the monomer from a signal having an intensity higher than the first threshold value, and setting a second threshold value of an intensity of a signal received from the pair of second electrodes according to a monomer molecule of a polymer and identifying the type of the monomer molecule from a signal having an intensity higher than the second threshold value. The first threshold value may be obtained from electrical signals from known monomer molecules using the pair of first electrodes. For example, a signal that efficiently distinguishes a specific monomer molecule may be selected as the threshold value among electrical signals of known monomer molecules obtained using the pair of first electrodes. As a result, a signal having a value lower than the first threshold value may not be used to identify the monomer molecule. In the same manner, the second threshold value may be obtained from electrical signals from known monomer molecules using the pair of second electrodes. For example, a signal that efficiently distinguishes a specific monomer molecule may be selected as the threshold value among electrical signals of known monomer molecules obtained using the pair of second electrodes. As a result, although each of the signals from the pair of first electrodes and the pair of second electrodes cannot individually distinguish all of the monomer molecules, all monomer molecules may be distinguished by combining the signals from the pair of first and the pair second electrodes. For example, the pair of first electrodes may include a graphene electrode. If a graphene electrode is used, the intensity of the tunneling current of four bases of DNA, i.e., A, T, G, and C may be detected in the order of G>T>>C>A. In addition, the pair of second electrodes may include a gold electrode. If a gold electrode is used, the intensity of the tunneling current of four bases of DNA, i.e., A, T, G, and C may be detected in the order of A>G>C>T. Thus, the first threshold value is set as a higher value than a signal value of C so that G and T may be distinguished from a signal value higher than the first threshold value. In this regard, G and T may be more efficiently distinguished by using a signal obtained according to the rotation or left-right shift of the polymer. Then, the second threshold value may be set as a higher value than a signal value of C so that A and G may be distinguished from a signal value higher than the second threshold value. In this regard, A and G may be more efficiently distinguished from each other by using a signal obtained according to the rotation or left-right shift of the polymer. Additionally, C, which is not analyzed, may be obtained by identifying A, T, and G by combining signals obtained from the pair of first electrodes and the pair of second electrodes, and determining an un-identified signal as C. These sequences may be determined by comparing passing time through the path.

The device for determining a monomer molecule sequence of a polymer according to the current embodiment may be used to efficiently determine a monomer molecule sequence of the polymer.

According to the method of determining a monomer molecule sequence of a polymer according to the current embodiment, the monomer molecule sequence of the polymer may be efficiently determined.

BRIEF DESCRIPTION OF THE DRAWINGS

These and/or other aspects will become apparent and more readily appreciated from the following description of the embodiments, taken in conjunction with the accompanying drawings of which:

FIGS. 7A-7D shows zero-bias transmission of DNA bases located between H-gap for the rotation of (7A) A, (7B) C, (7C) G, and (7D) T from −90° to +90° by steps of 30°;

DETAILED DESCRIPTION

Figure 1:
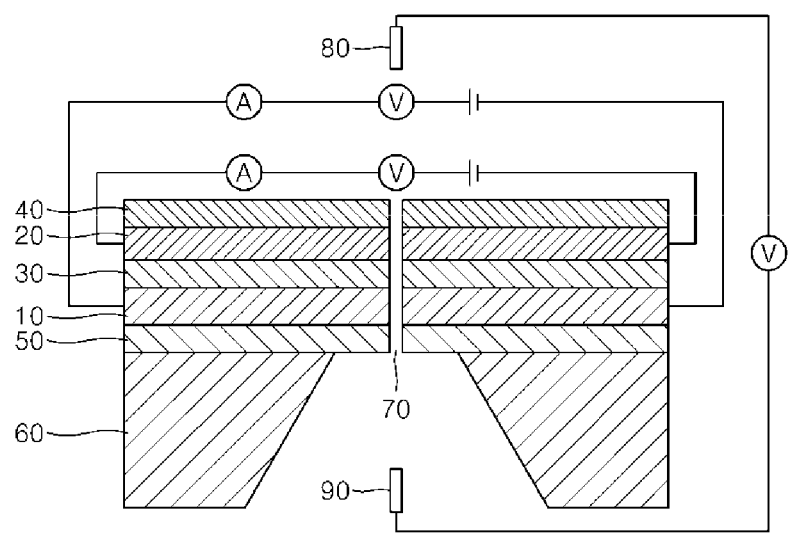
FIG. 1 shows a device for determining a monomer molecule sequence of a polymer.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Example 1

Device for Determining Monomer Molecule Sequence of Polymer

FIG. 1 shows a device for determining a monomer molecule sequence of a polymer according to an embodiment of the present invention.

Referring to FIG. 1, the device for determining a monomer molecule sequence of a polymer includes: a pair of first electrodes 10 that are formed of a first material and separated from each other by a gap 70 disposed therebetween; a pair of second electrodes 20 that are separated from each other by the gap 70 disposed therebetween and formed of a material having one or more electrical characteristics that are different from the electrical characteristics of the material of the first electrodes 10, in which the first electrodes 10 and the second electrodes 20 are separated by a pair of insulating materials 30 that are separated from each other by the gap 70. The gap 70 disposed between each of the first and second pair of electrodes and the pair of insulating materials forms a passage through the stacked layers. In other words, the gaps or separations between each of the electrodes of the first pair, the electrodes of the second pair, and the pair of insulating materials are stacked in alignment with each other to form a path through which a polymer moves. The device may further include electrical signal detectors A or V respectively connected to the first electrodes and the second electrodes; a polymer positioning unit 80 and 90 for disposing the polymer in the path; and a polymer moving unit for rotating or left-right shifting the polymer disposed in the path. The polymer positioning unit 80 and 90 for disposing the polymer in the path may be a pair of electrodes for providing a voltage bias at both ends of the path. Insulating materials 30, 40, and 50 may be disposed on the lower surfaces of the first electrodes 10 and the upper surfaces of the second electrodes 20 as well as between the first electrodes 10 and the second electrodes 20, as shown in FIG. 1. The device may be supported by a support substrate 60. The support substrate 60 may be formed of silicon, and the insulating materials 30, 40, and 50 may be silicon nitride. The device shown in FIG. 1 may be prepared by using a known method of preparing a micro structure, for example, photolithography.

Figure 2:
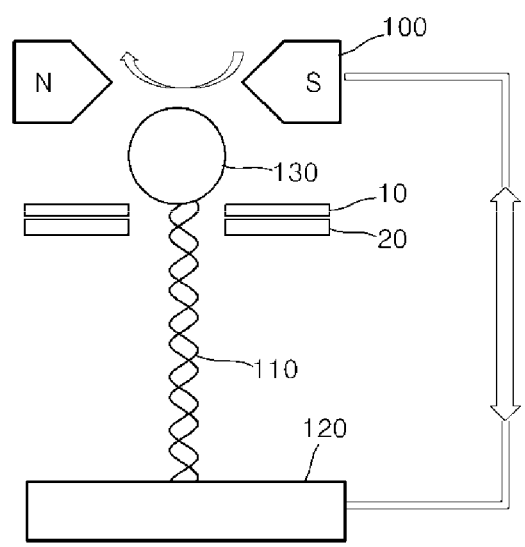
FIG. 2 shows a device for determining a monomer molecule sequence of a polymer.

FIG. 2 shows a device for determining a monomer molecule sequence of a polymer according to another embodiment of the present invention. FIG. 2 shows a portion of the device of FIG. 1 and elements added thereto. Referring to FIG. 2, one end of the polymer (e.g., nucleic acid) 110 is bound to a substrate 120, and the other end thereof is bound to a nanoparticle or microparticle 130. The nanoparticle or microparticle 130 may be a magnetic particle or magnetic bead. The polymer, e.g., nucleic acid 110 may be rotated, be left-right shifted, or moved in the longitudinal direction along the path by a tweezer, e.g., a magnetic tweezer. The rotation or left-right shift may be performed by a rotation or left-right shift of the tweezer, e.g., a magnetic tweezer 100. In addition, moving in the longitudinal direction along the path may be performed by relative movements of the tweezer, e.g., a magnetic tweezer 100 and the substrate 120. During the rotation, left-right shift, or movement in the longitudinal direction along the path, electrical signals according to a travel angle or distance may be detected by using an electrical signal detector (A or V) (see FIG. 1). The detected electrical signal may be processed by using a signal processor (not shown) connected to the electrical signal detector (A or V). The tweezer may be an optical tweezer. The optical tweezer may move transparent dielectrics having a high refractive index by irradiating focused light to the transparent dielectrics. The nanoparticle or microparticle 130 may be a transparent dielectric. In addition, the nanoparticle or microparticle 130 may be moved up and down and left and right directions, or the structure of the electrode may be relatively moved, using a piezo-control.

In the device of FIG. 2, the magnetic tweezer or optical tweezer may be a known tweezer. In addition, the electrical signal may be detected, for example, by using an Axopatch that is used to measure a micro electrical signal of a cell membrane. The device may further include a data processor that calculates an average of real-time current values of the measured signal during one rotation.

By using a device according to an embodiment of the present invention, a base sequence of a nucleic acid may be classified by using only two types of electrodes. In addition, since, in a single polymer molecule, the monomer molecule sequence of the polymer may be determined by using a current value according to a rotation angle as well as current values at a predetermined position through statistical sample processing, reliability of an obtained sequence may be increased. If a control device such as a tweezer is used, movement or speed of nucleic acid strands may be controlled. In addition, since the polymer, e.g., nucleic acid may be spread by using the tweezer, the monomer molecule sequence of the polymer such as a nucleic acid may be measured in a non-electrolytic solution such as water as well as an electrolytic solution, and noise caused by ions generated during the measurement may be reduced.

Example 2

Calculation of Current According to Base of DNA Passing between Zigzag Graphene Nanoribbon Electrodes DNA was passed through a gap of a device for determining a monomer molecule sequence of a polymer including a pair of first electrodes that are formed of a first material and separated from each other by the gap therebetween, and current according to the bases of DNA was calculated by a quantum tunneling simulation. The interval (gap) between the electrodes was 1 nm, and the first electrodes were zigzag graphene nanoribbon electrodes. The gap is disposed in a membrane having an open side in one direction. The current was measured by calculating current according to the rotation of the bases of DNA while applying 1 V of a bias voltage across the gap between the first electrodes. A quantum transport current was calculated by using Landauer Equation 1 below. In Equation 1, V is a bias voltage, T(V,E) is an electron transmission probability, f(E-μ) is a Fermi-Dirac distribution function with respect to energy E based on a chemical potential μ, e is a charge of a single electron, and h is the Plank constant.

$$I(V) = \frac{2e}{h} \int_{\mu_R}^{\mu_L} T(V, E)[f(V - \mu_L) - f(E - \mu_R)] dE \quad (1)$$

Figure 3A:
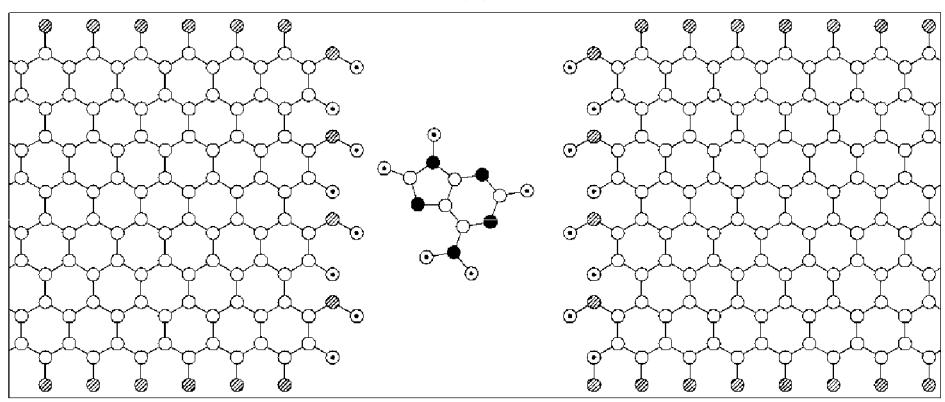
FIGS. 3A to 3E show bases of nucleotides that are positioned in a gap between graphene electrodes.
Figure 3B:
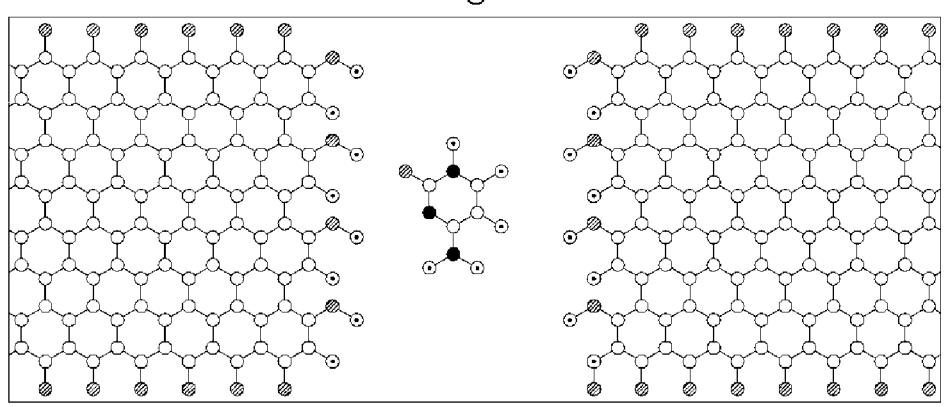

For a calculation using Equation 1, a TranSIESTA module of Siesta simulation package including a density functional theory-nonequilibrium Green's function (DFT-NEGF) was used. In this regard, DFT was calculated by considering GGA-PBE, double zeta-polarized (DZP) for basis of all atoms, and 100 Ry cutoff energy. For example, a system or variable used in the calculation at a reference angle of G is shown in FIG. 3B.

FIGS. 3A to 3E show bases of nucleotides that are positioned in a gap between graphene electrodes. In FIG. 3A to 3D, A, C, G, and T respectively refer to adenine, cytosine, guanine, and thymine, which are bases of DNA showing shapes of the bases at a standard position where a rotation angle is 0. If the base is rotated in a clockwise direction at the standard position, a negative (−) rotation angle was provided thereto. If the base is rotated in counter-clockwise direction, a positive (+) rotation angle was provided thereto.

Figure 3C:
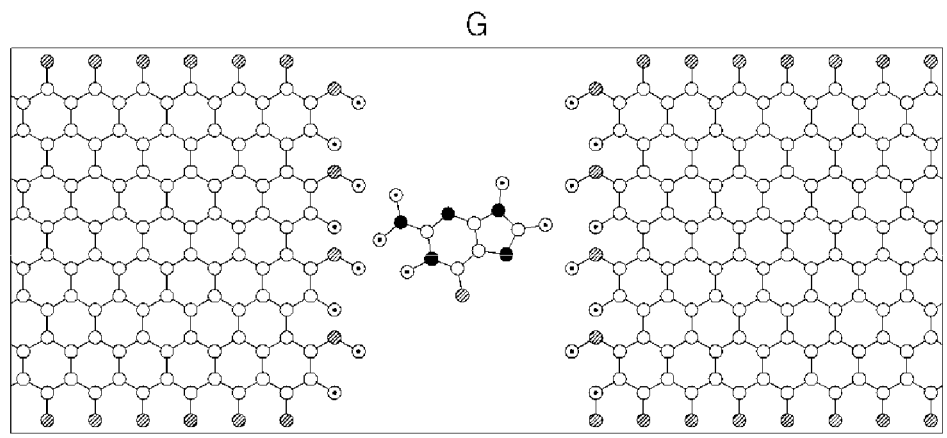
Figure 3D:
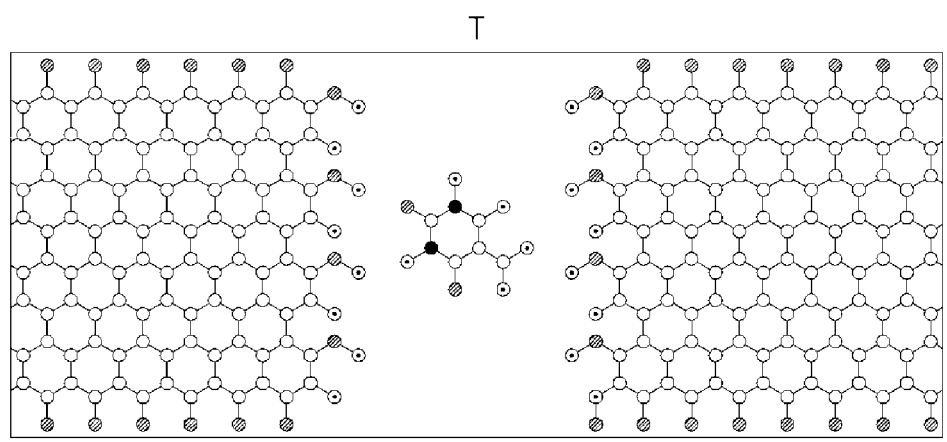
Figure 3E:
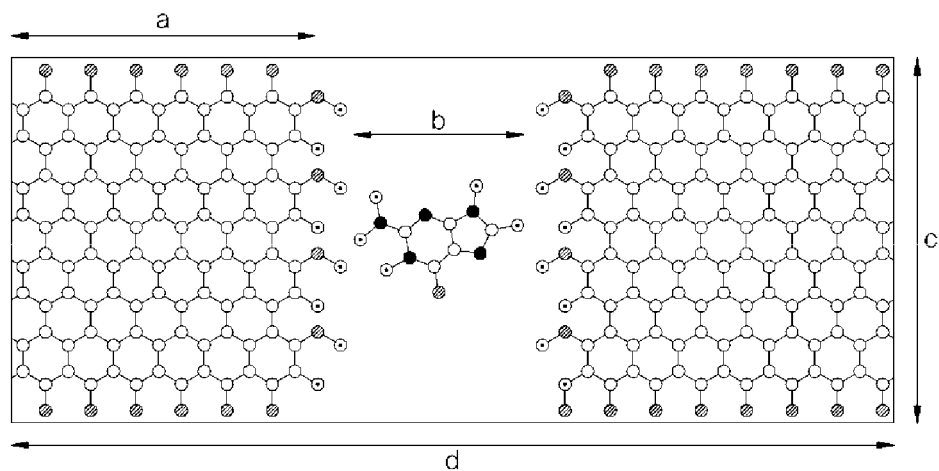

FIG. 3E shows a system or variable used in the calculation at a reference angle of G of FIG. 3C. In FIG. 3E, an arrow "a" shows a length of graphene at a portion other than the gap of 1.68 nm formed of six unit cells. Among the six units, two units were used in a calculation of electrodes repeated by periodic boundary condition along the z axis. The K-points are set as 51. Here, an arrow "b" shows that a diameter of the gap is 1 nm, an arrow "c" shows that a longitudinal length of the path of the graphene electrode is 1.84 nm, and an arrow "d" shows that the entire length of the system in the electrode direction including the gap is 4.47 nm. In FIG. 3A to 3E, ⊛ indicates oxygen, ⊙ indicates hydrogen, ● indicates nitrogen, and ○ indicates carbon.

Figure 4:
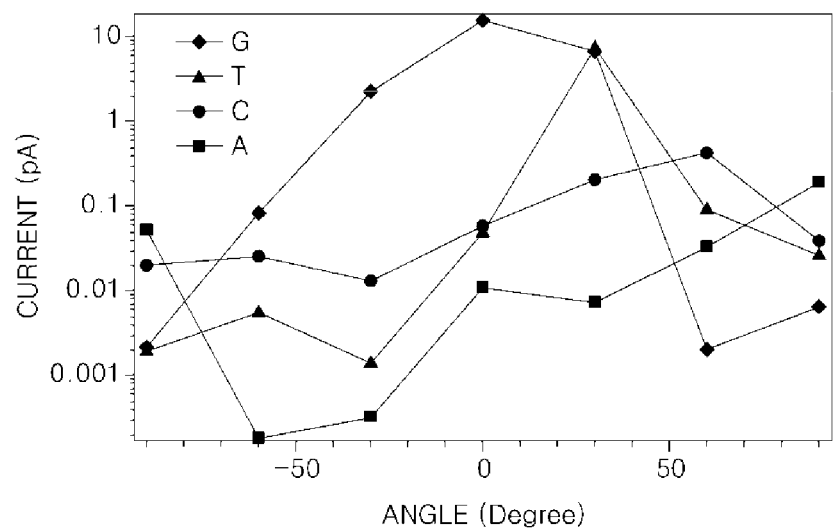
FIG. 4 is a graph illustrating variation of current values with respect to rotation of DNA.

FIG. 4 is a graph illustrating variation of current values with respect to rotation of DNA. The rotation was conducted from −90° to +90°. Although the bases are not distinguished from each other at a predetermined position, values obtained by integrating the current value with respect to the rotation angle and calculating an average thereof may be distinguished from each other. In this manner, the base sequence of DNA may be determined by measuring current values at predetermined positions and calculating an average of the current values according to the rotation angle. The range of the rotation angle may be appropriately selected according to types of the electrode, combinations thereof, types of selected nucleic acids, and the like, for example, −30 to +30, −60 to +60, and −90 to +90.

(1) EXPERIMENTAL METHOD

Figure 5:
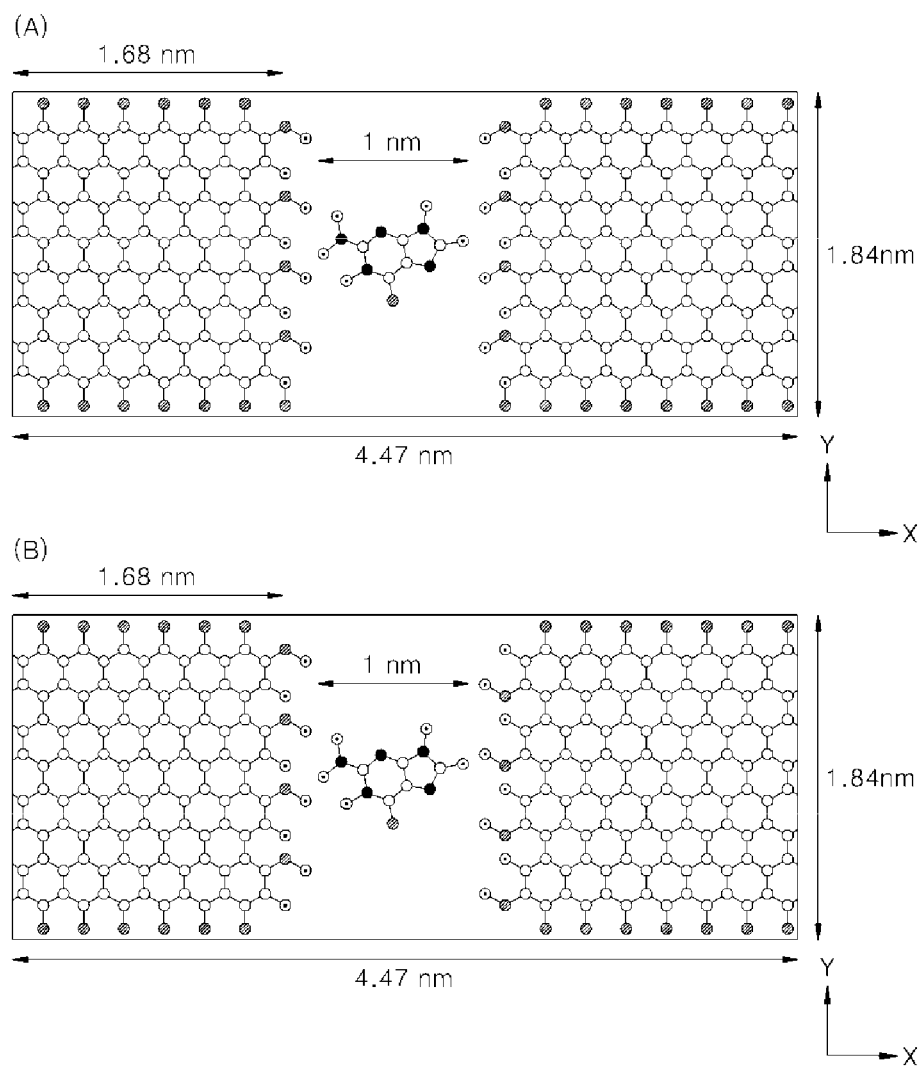
FIG. 5 shows two types of gap edge terminated ketone-zigzag graphene (ZGNR) electrodes.
Figure 6A:
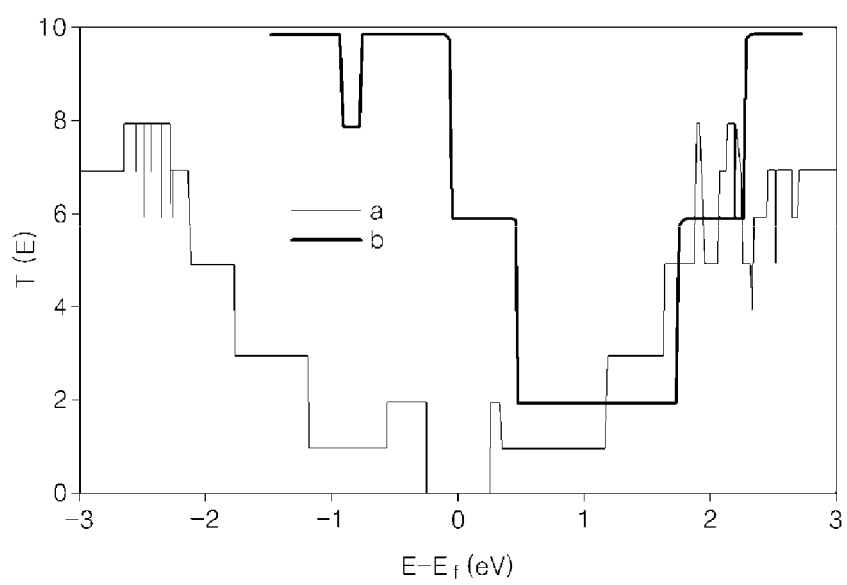
FIGS. 6A-6I shows a comparison of conductance between H-ZGNR and ketone-ZGNR.
Figure 6B:
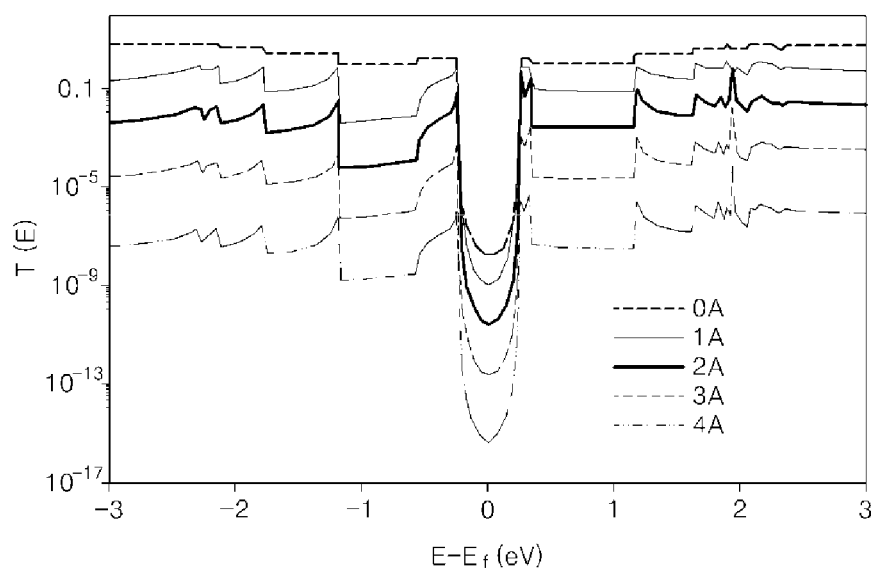
Figure 6C:
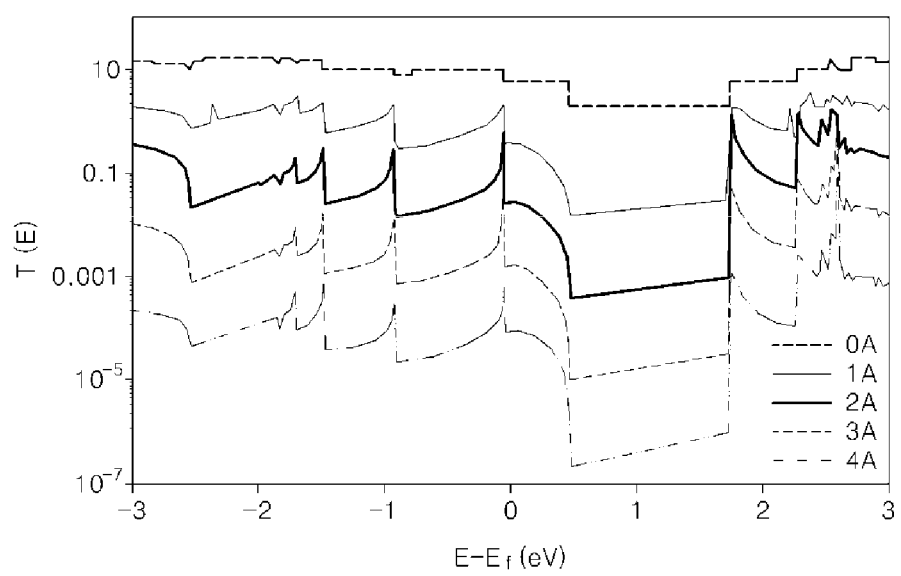
Figure 6D:
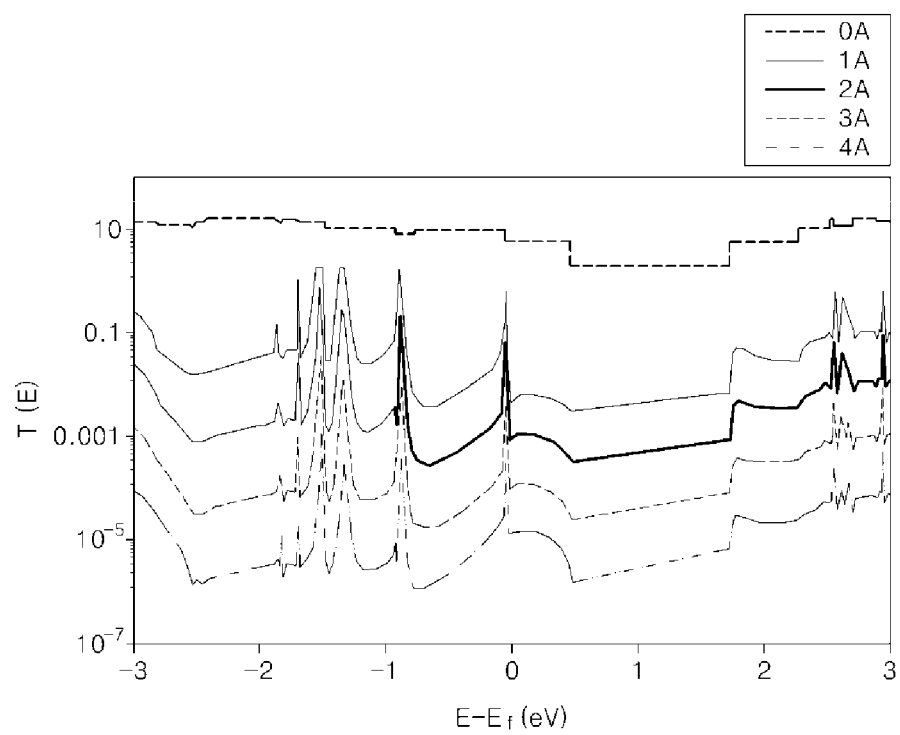
Figure 6E:
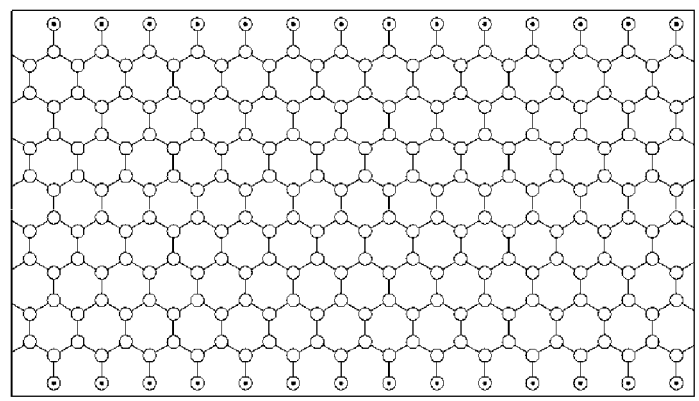
Figure 6F:
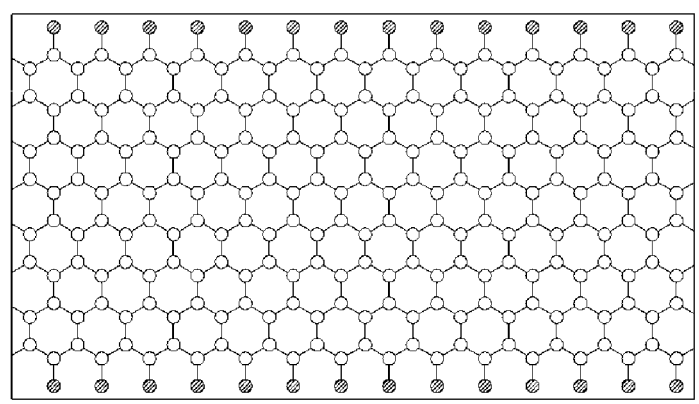
Figure 6G:
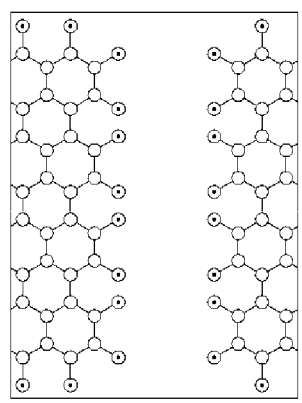
Figure 6H:
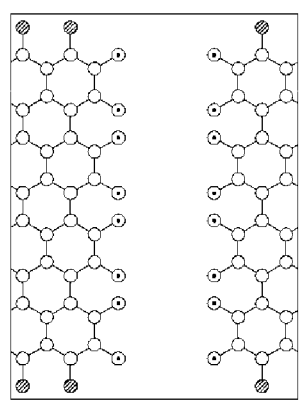
Figure 6I:
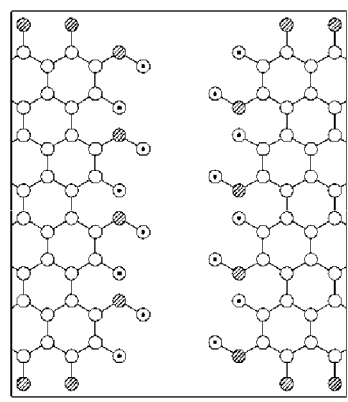

The dramatic changes in the shape and the magnitude of transverse conductance of each DNA base were investigated by focusing on zero-bias transmission T(E) at Fermi-energy and transmission dips originated from destructive quantum interference (DQI). As DNA bases rotate or translate with respect to the electrode, quantum interference affects the tunneling conductance of each base either constructively or destructively. FIG. 5 shows two types of gap edge terminated ketone-zigzag graphene (ZGNR) electrodes. FIG. 5A shows a symmetric ketone-hydroxyl gap-edge, and FIG. 5B shows an asymmetric ketone-hydroxyl gap-edge. In FIGS. 5A and 5B, ◉ indicates oxygen, ⊙ indicates hydrogen, ● indicates nitrogen, and ○ indicates carbon. A nanopore-edge ZGNR pair of a mirror symmetric configuration of FIG. 5A is referred to as cis, and a nanopore-edge ZGNR pair of an asymmetric configuration of FIG. 5B is referred to as trans.

FIG. 6 shows comparison of conductance between H-ZGNR and ketone-ZGNR. FIG. 6A shows a complete zigzag graphene (ZGNR) with respect to two different zigzag-edges. The line indicates conductance of H-terminated ZGNR as illustrated in FIG. 6E, and the line b indicates conductance of O-terminated ZGNR as illustrated in FIG. 6F. When the center of the complete zigzag graphene (ZGNR) was cut, armchair-gap edges are formed with either (b) H-terminated as illustrated in FIG. 6G or (c) O-terminated as illustrated in FIG. 6H. FIGS. 6B and 6C show conductance of the obtained zigzag graphene (ZGNR) electrode, that is, (b) H-terminated as illustrated in FIG. 6G or (c) O-terminated as illustrated in FIG. 6H. FIG. 6D indicates electrical conductance O-zigzag edge/ketone-hydroxy terminated gap-edge as illustrated in FIG. 6I with respect to other distances. In FIG. 6, the ◉ indicates oxygen, the ⊙ indicates hydrogen, and the ○ indicates carbon.

To investigate the transverse conductance of DNA bases located between ZGNR of the nanopore, a unit cell composed of 16 carbon atoms and two oxygen atoms was first optimized. By extending unit cell by 14-fold, a unit cell consisting of 16 carbon atoms and 2 oxygen atoms was optimized. By extending the unit cell by 14 times, ZGNR was constructed and then separated by two parts with 1.65 nm in length and 1.84 nm in width. Both edges were terminated by OH or H alternatively to form either "cis" or "trans" type. Nanopore-ZGNR pairs were initially separated from each other for 2 nm for relaxation. The optimized half was relocated to form a final coordinate of 1 nm. Consequently, the dimensions of a super-cell for the system of ZGNR electrodes were 41.92 nm×25 nm×4.59 nm in x, y, and z direction. The z axis was chosen for the direction of transverse currents and transports. Finally, four DNA bases—adenine (A), guanine (G), cytosine (C), and thymine (T)—were placed inside a 1 nm gap between the two electrodes.

Orientations of each base were rotated around the normal axis (y) with respect to the plane (x-z) from 90 to −90 degrees in steps of 30 degrees. All optimizations were done based on density functional theory (DFT, GGA-PBE) implemented in the SIESTA package. Double zeta-polarized (DZP) basis were employed for all atoms and 100 Ry was considered as cutoff energy. For the quantum transport calculation, the present inventors adapted DFT based NEFG formalism implemented in a TranSIESTA module of the SIESTA package based on the Landauer approach.

(2) BASE ANGLE DEPENDENT CONDUCTANCE

Before our discussion on cis/trans OH/H-gap functionalization, zero-bias transmission T(E) of A, C, G and T for H-gap ketone-ZGNR was first investigated as a reference. FIG. 7 shows zero-bias transmission of DNA bases located between H-gap for the rotation of (a) A, (b) C, (c) G, and (d) T from −90° to +90° by steps of 30°.

Figure 7B:
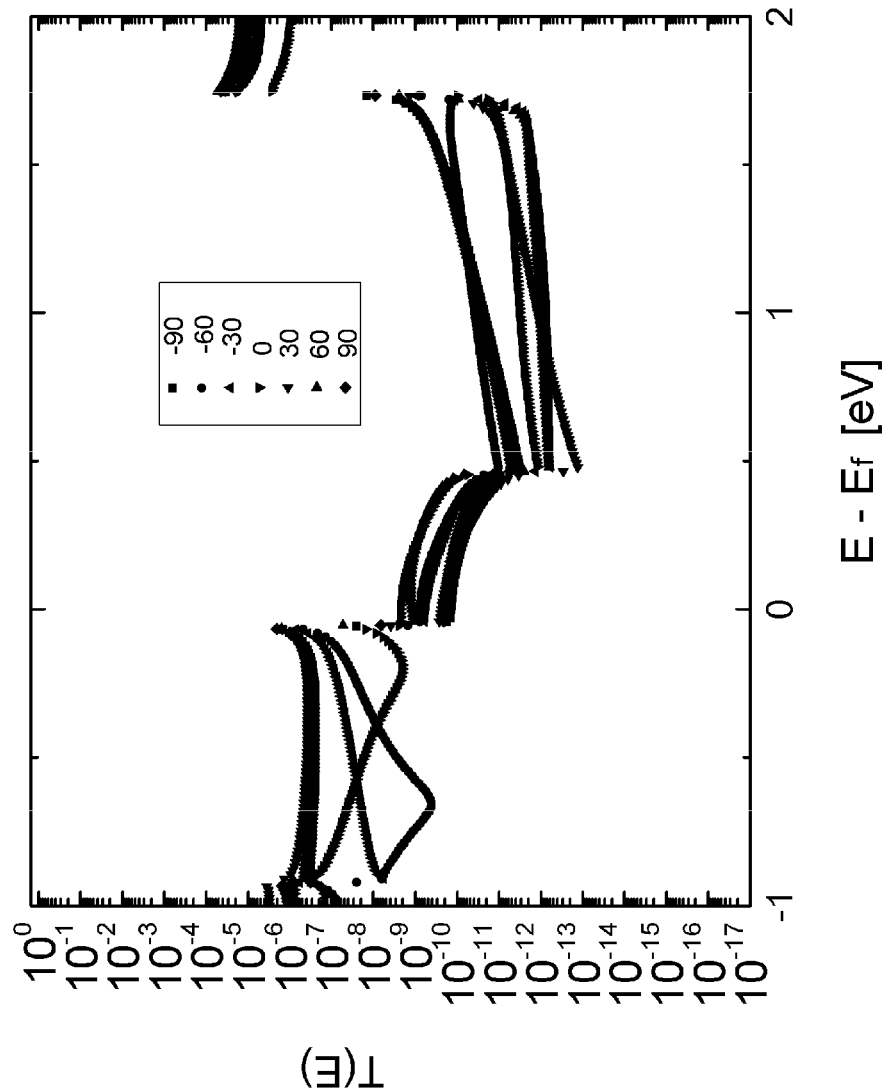
Figure 7C:
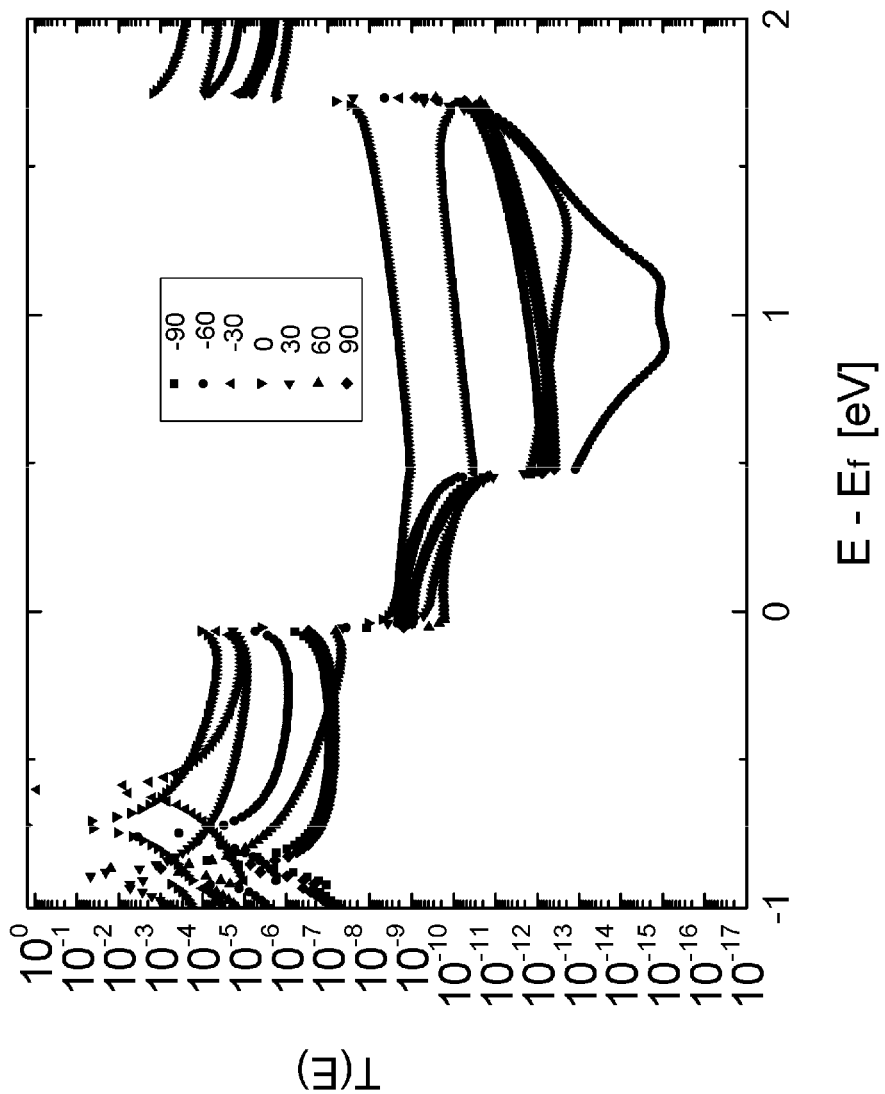

For the case of A, transmissions near Fermi-level vary within an order of magnitude (FIG. 7A). On the other hand, transmissions for G are fluctuated by two orders of magnitude (FIG. 7C). Origin of the fluctuation can be interpreted as strong coupling effects between G and the electrode as shown in the frontier HOMO peak shifts. By considering Fermi-energy of the total system (−4.88 eV) and frontier HOMO energy-level of isolated G (−5.36 eV) the amount the energy shifts occur by Δmin~0.08 eV<Δ<Δmax~0.35 eV (FIG. 7C). Note the minimum energy shifts Δmin occurred for the 30° rotation with respect to the reference (0°), and the shift seems to be correlated with the large coupling rate, Γmax, as indicated by the broadened peak. The minimum coupling rate Γmin for −30° rotation, however, obviously correlated with the Δmax. Most of all, T(Ef) has maximum values for the case of the reference, at which large shift of frontier energy level (Δ~0.3 eV) and large coupling rate Γ(FWHM)~0.1 eV occur. Therefore, the reference direction provides optimum self-energy for transmission through guanine.

Figure 7D:
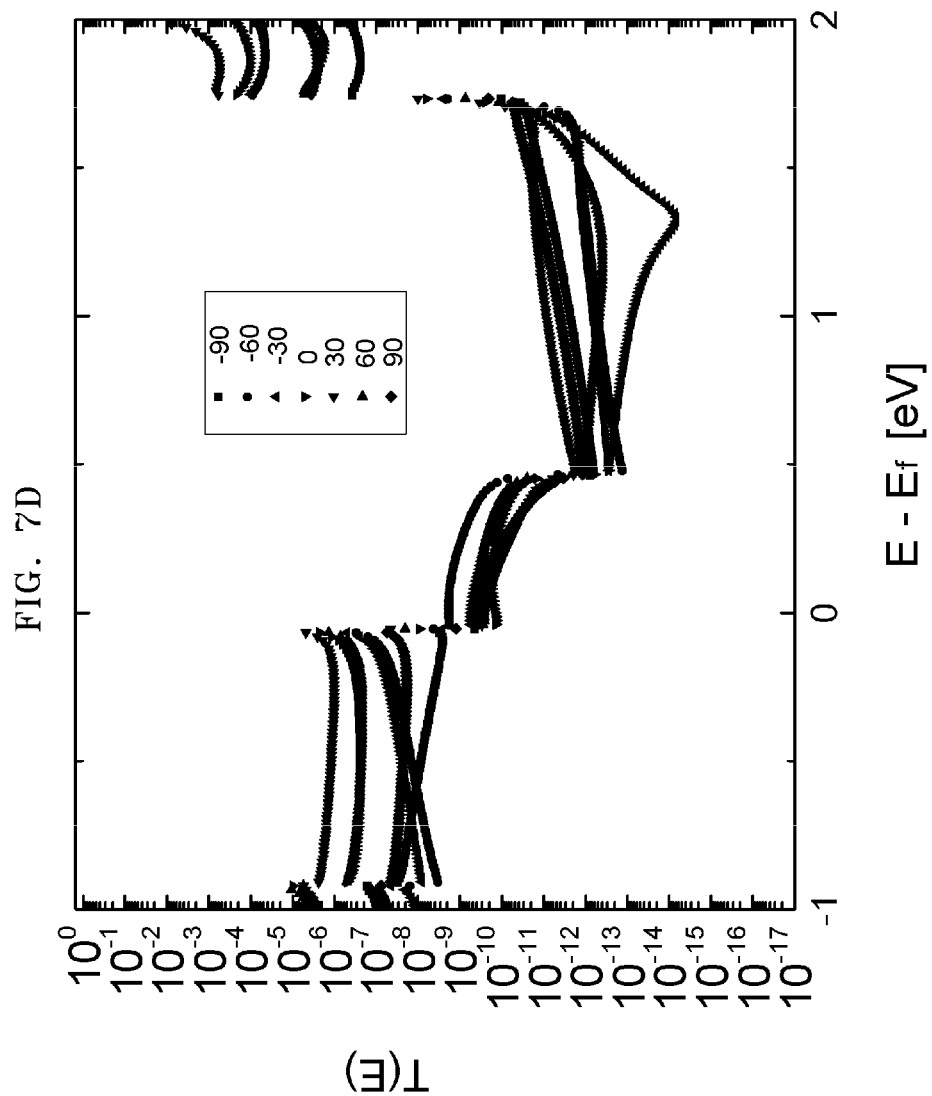
Figure 8A:
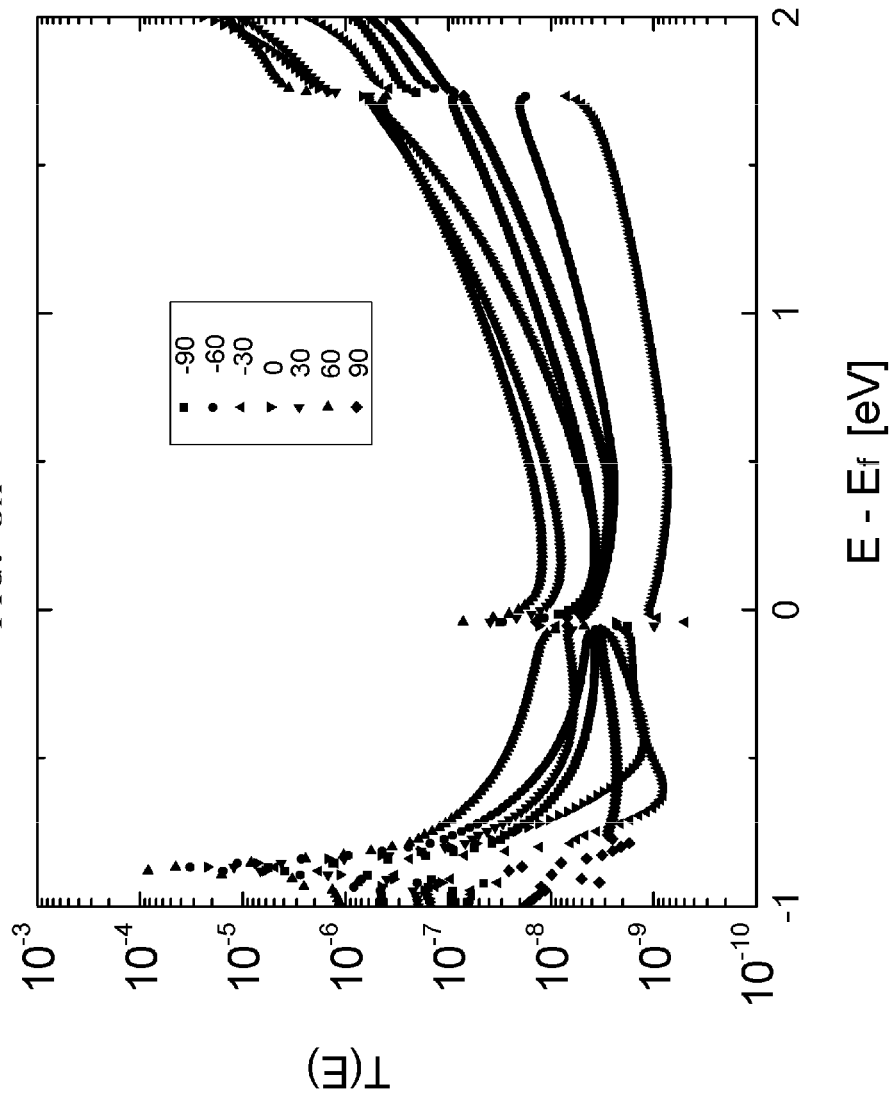
FIGS. 8A-8D shows zero bias transmission of DNA bases located between "cis" OH/H-gap-edges for the rotation of (8A) adenine, (8B) cytosine, (8C) guanine, and (8D) thymine from −90° to 90° by steps of 30°.
Figure 8B:
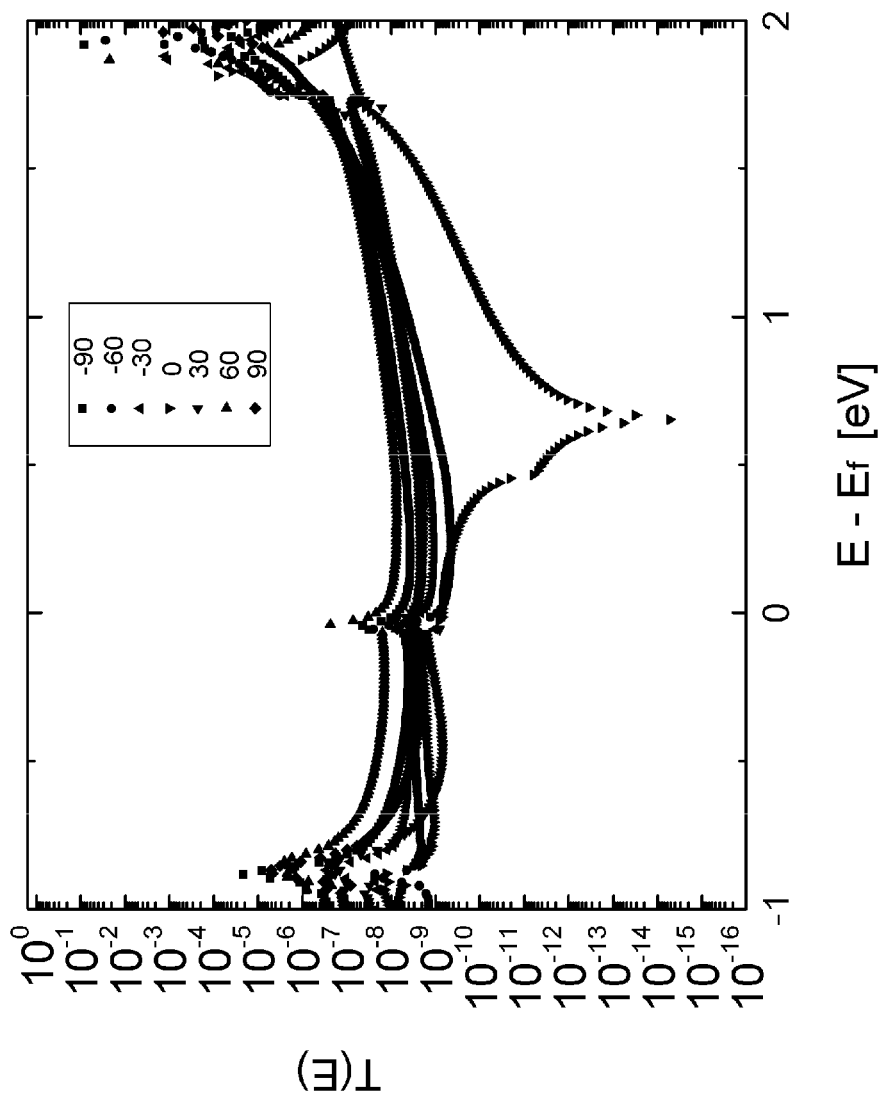
Figure 8C:
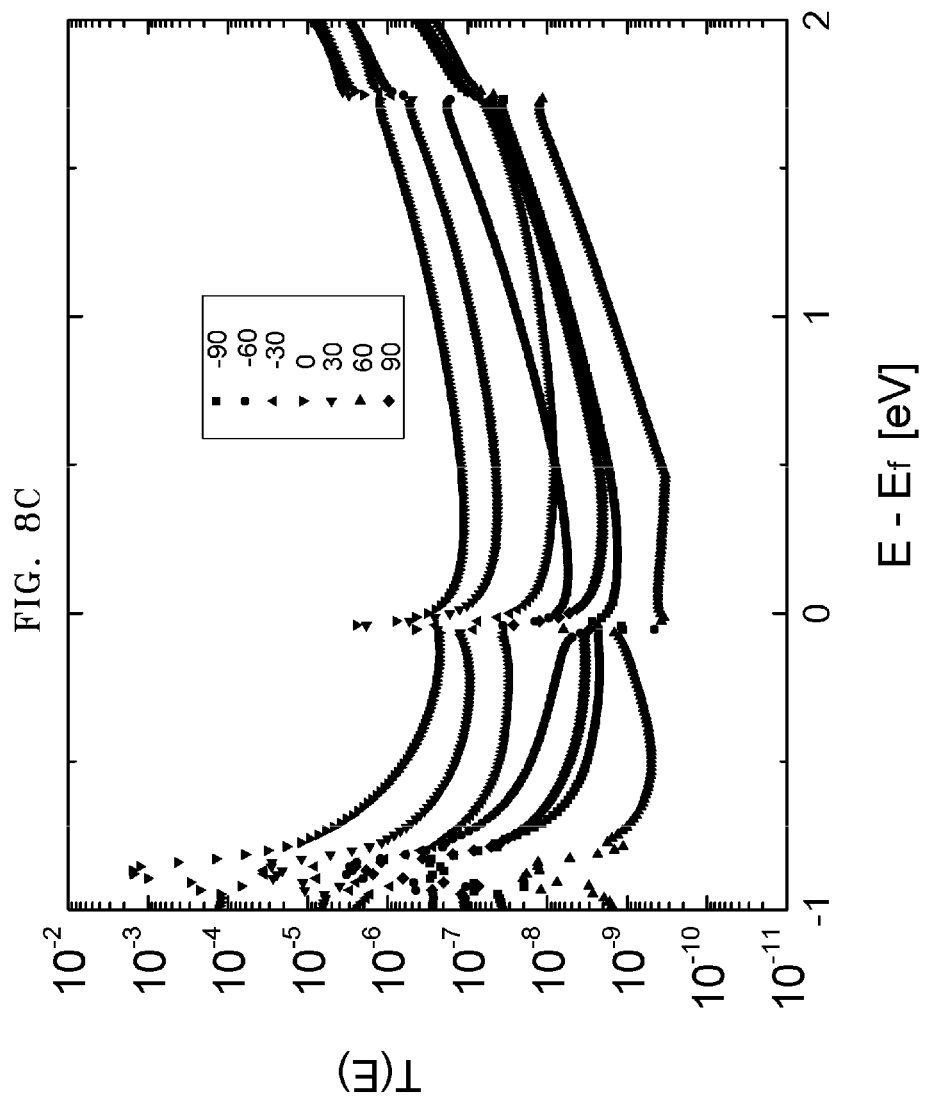
Figure 8D:
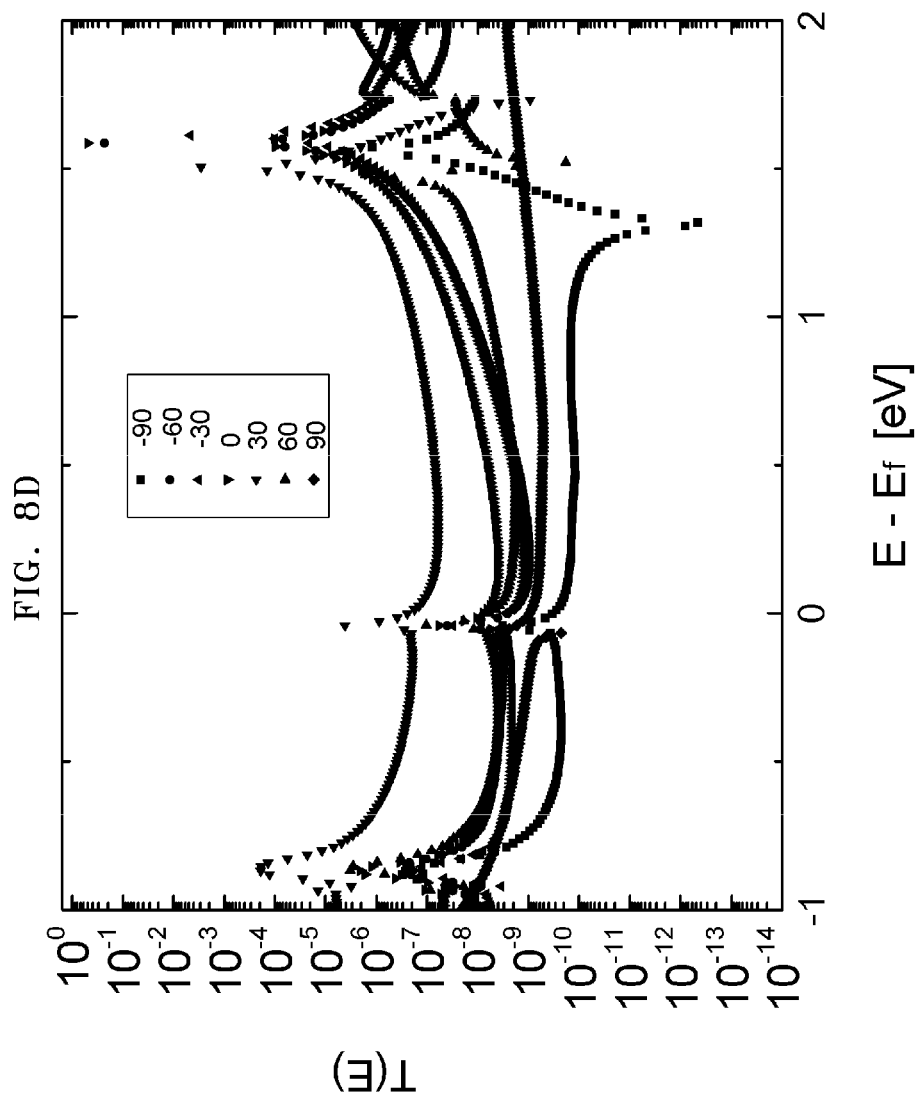

Transmission through C varies by three orders of magnitude depending on base angle. (FIG. 7B). On the other hand, the T(Ef) only varies within an order of magnitude for the case of T, as seen in FIG. 7D. The difference between C and T is the number of oxygen atoms, i.e. C or G has one oxygen atom, but T has two. This indicates that electron density of T can be evenly distributed by two oxygen atoms.

To demonstrate conductance through A, C, G, and T in realistic cis[trans]-type OH/H gap-termination, transmissions are calculated as in FIGS. 8 and 9. FIG. 8 shows zero bias transmission of DNA bases located between "cis" OH/H-gap-edges for the rotation of (a) adenine, (b) cytosine, (c) guanine, and (d) thymine from −90° to 90° by steps of 30°. FIG. 9 shows zero bias transmission of DNA bases located in "trans" OH/H-gap for the rotation of (a) adenine, (b) cytosine, (c) guanine, and (d) thymine from −90° to 90° by steps of 30°.

Figure 9A:
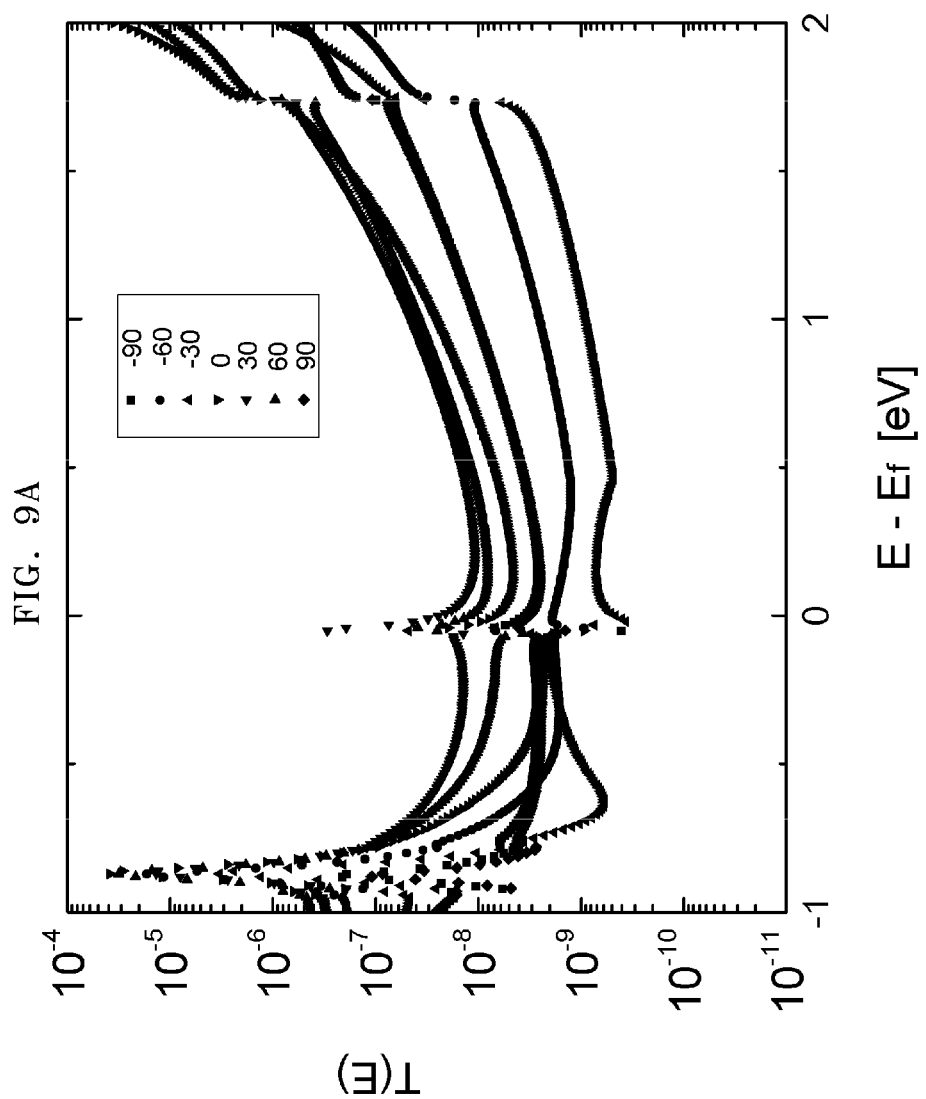
FIGS. 9A-9D shows zero bias transmission of DNA bases located in "trans" OH/H-gap for the rotation of (9A) adenine, (9B) cytosine, (9C) guanine, and (9D) thymine from −90° to 90° by steps of 30°.
Figure 9B:
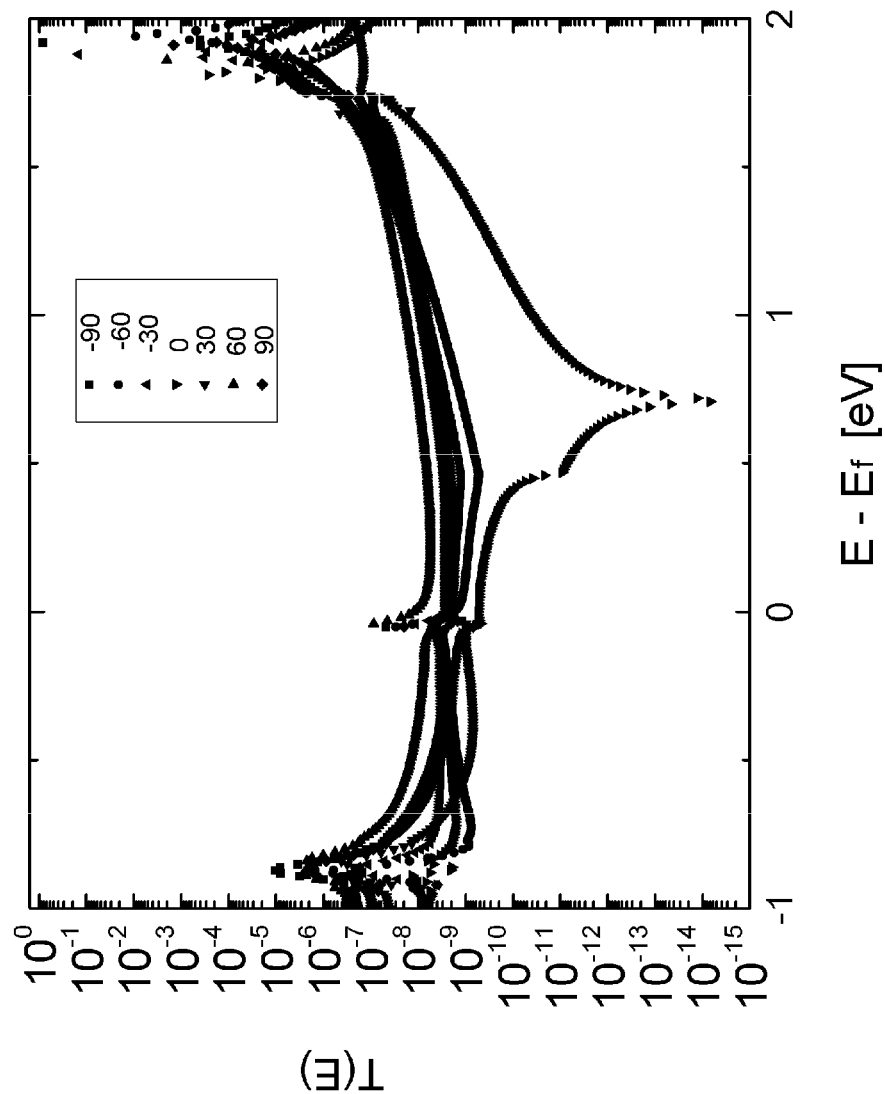
Figure 9C:
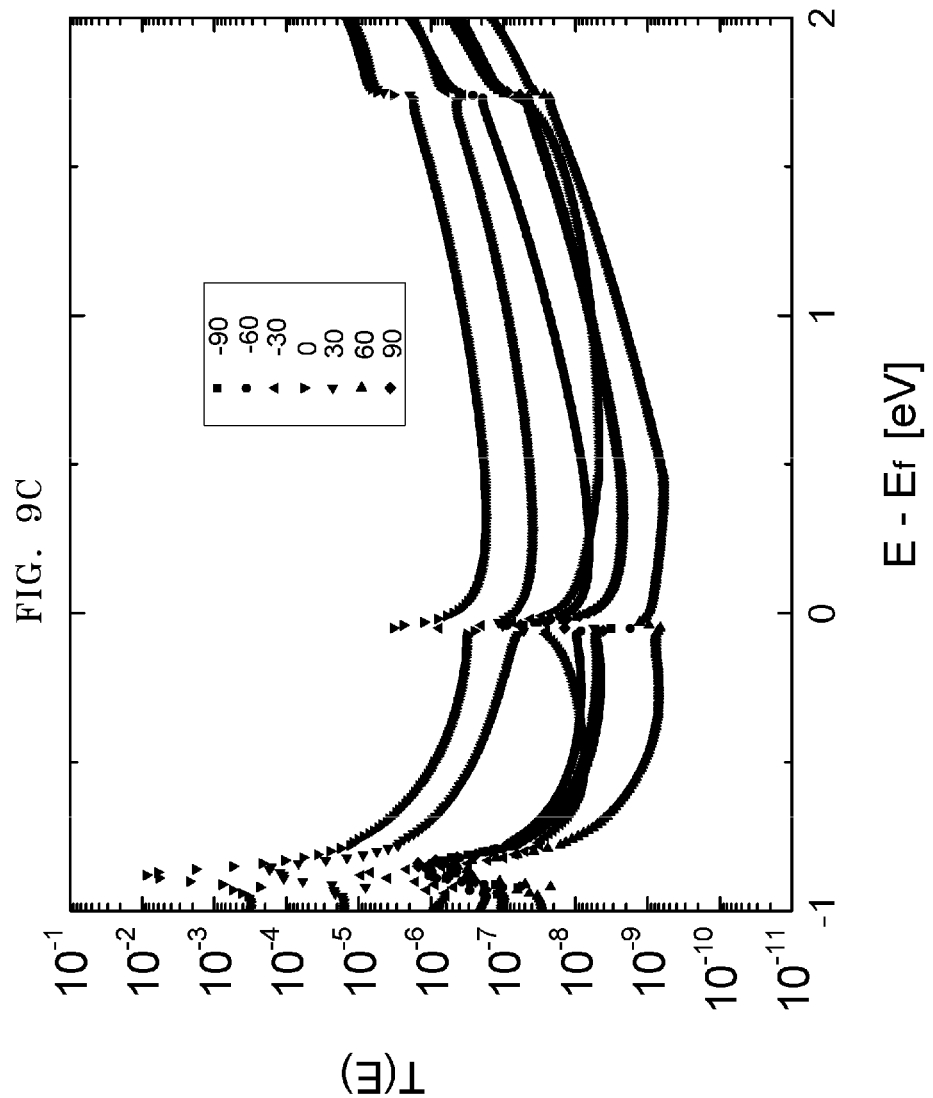
Figure 9D:
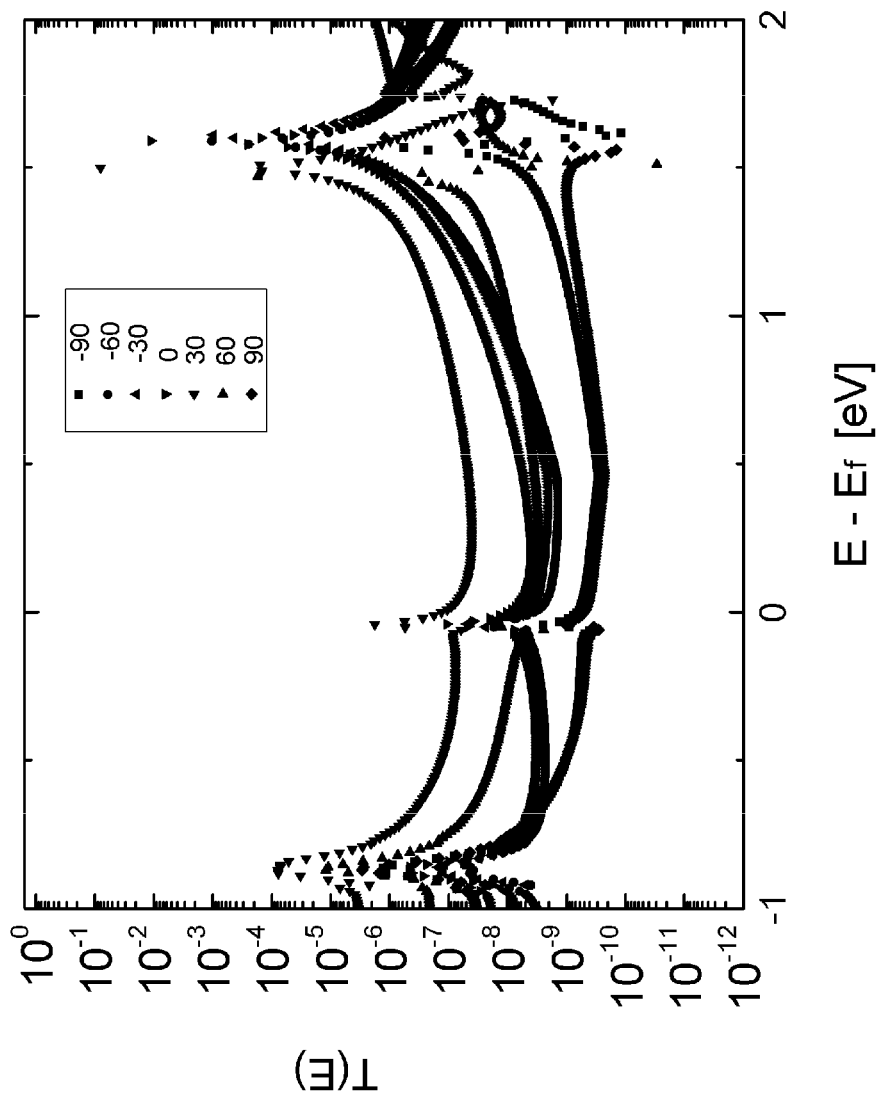

Both cis and trans-type transmission show similar magnitude and shape including a dip near 0.5 eV above Ef for the case of G. Both show no van-hove singularities because of the smooth chemical termination of ZGNR edges. The only difference between "cis" and "trans" is the existence of a dip in the transmission. For example, C has a dip −60° in "trans"-type OH/H-gap (FIG. 9B). Despite the chemical identity, a mirror asymmetric position of the OH/H-gap in the right electrode significantly alters the quantum phase, especially for the pyrimidine ring. This indicates that purine conserves quantum phase of the left electrode until it reaches the right electrode.

Figure 10A:
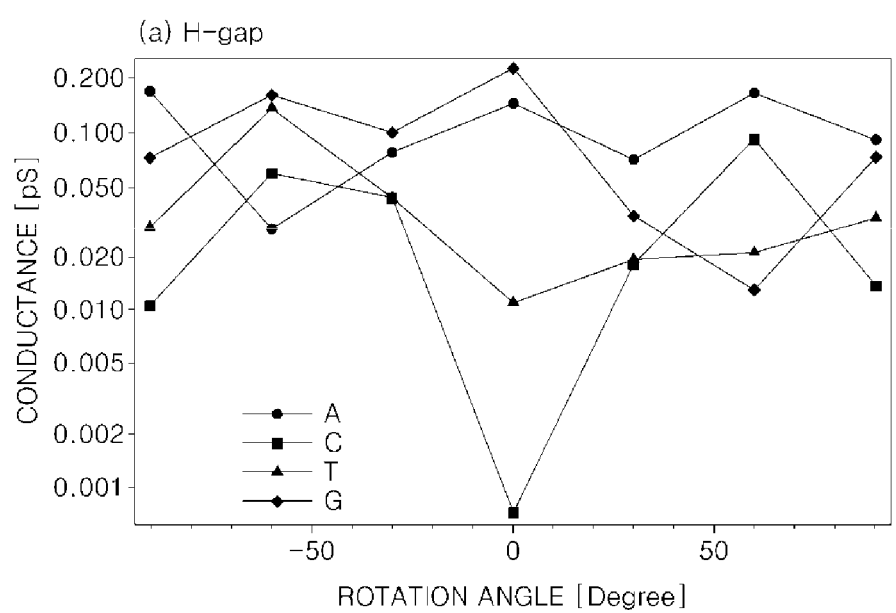
FIGS. 10A-10C shows zero bias conductance of four DNA bases located between (10A) H-terminated gap-edges, (10B) cis-type OH/H-terminated gap-edges, and (10C) trans-type OH/H-terminated gap-edges.
Figure 10B:
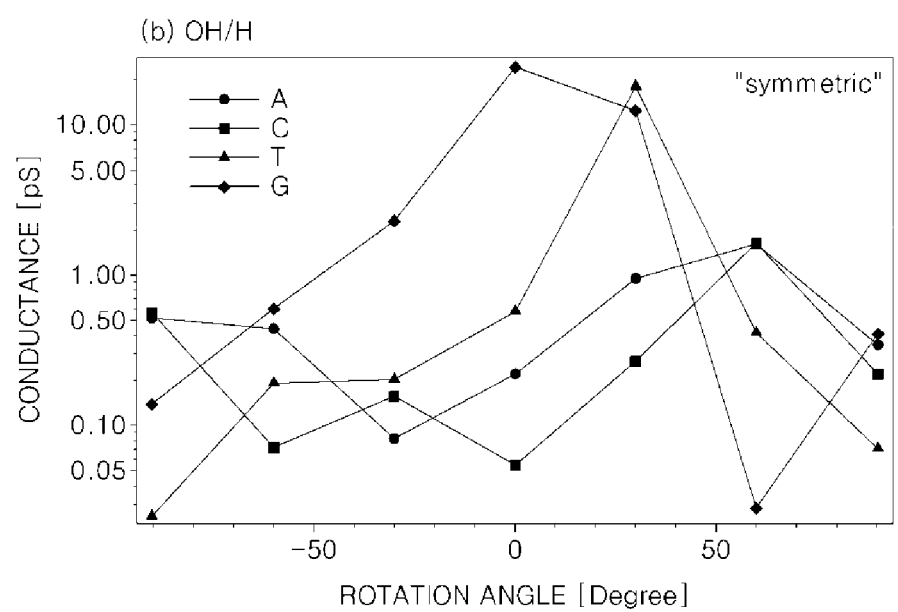
Figure 10C:
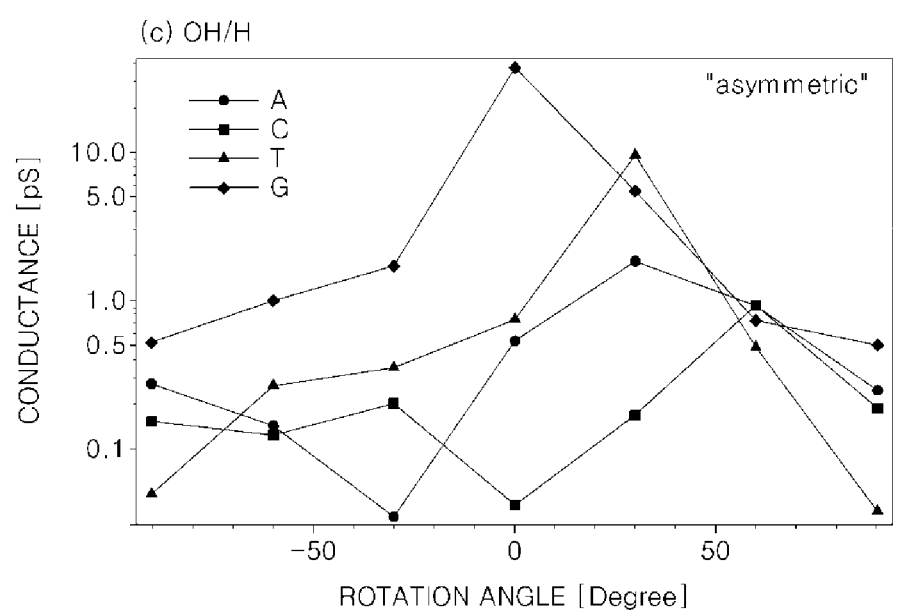

From above transmission data, conductance was obtained at Fermi-energy which is directly proportional to the magnitudes of tunneling currents for different angles of DNA bases. (FIG. 10). FIG. 10 shows zero bias conductance of four DNA bases located between (a) H-terminated gap-edges, (b) cis-type OH/H-terminated gap-edges, and (c) trans-type OH/H-terminated gap-edges.

Despite the hierarchy in the current magnitudes for 0°: G>A~T>C, the value of zero-bias transmission varies due to rotation of angles from −90° to 90° with steps of 30° and to the three different gap-edge termination types (a), (b) and (c) from above. By the estimation from T(Ef), the maximum tunneling current turns out to be about tens of pA level at 1V bias voltage for G at its reference angle (0°). There is a three orders of magnitude larger enhancement when it is compared to tens of fA level currents evaluated for H-terminated armchair-gap edge graphene electrodes.

The OH/H-gap also provides transmissions for all four DNA bases by about an order of magnitude higher than H-gap. Thus, from now on, only "cis" or "trans" OH/H-gap termination will be considered for further analysis. The enhancements in currents exploit the metallic ketone-terminated ZGNR. Despite the metallic electrode properties, except for G and T, most of the currents would be less than a few pA so that it is difficult to distinguish bases.

(3) TRANSMISSION DIP

To investigate physical differences among four bases further, additional transmission dips were searched by rotating bases in steps of 5° from the angle where a dip exists in FIGS. 8 and 9. The dip was originated from destructive quantum interference (DQI).

Figure 11A:
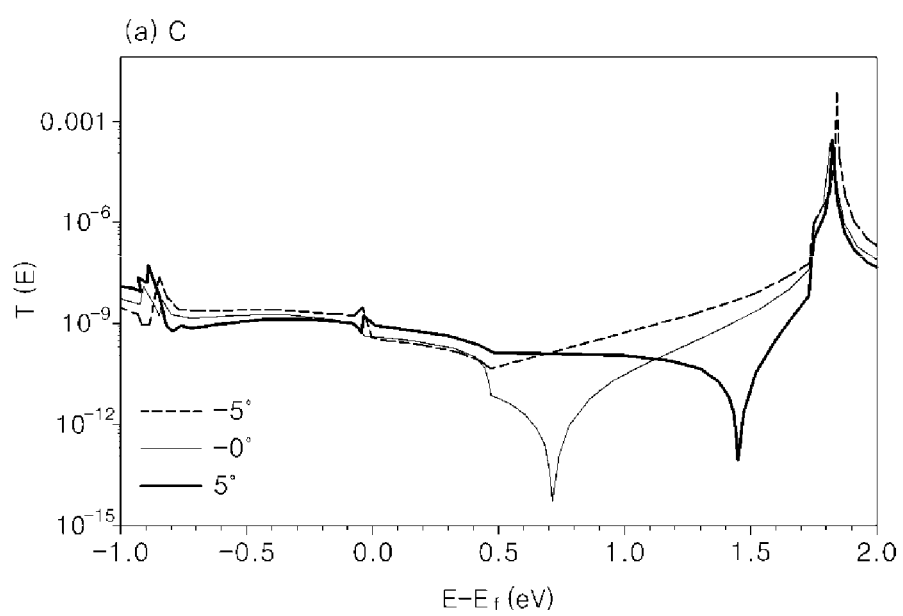
FIGS. 11A-11B shows zero bias transmission of DNA bases located in "cis" OH/H-gap for the rotation of (11A) cytosine and (11B) guanine in steps of 5°.
Figure 11B:
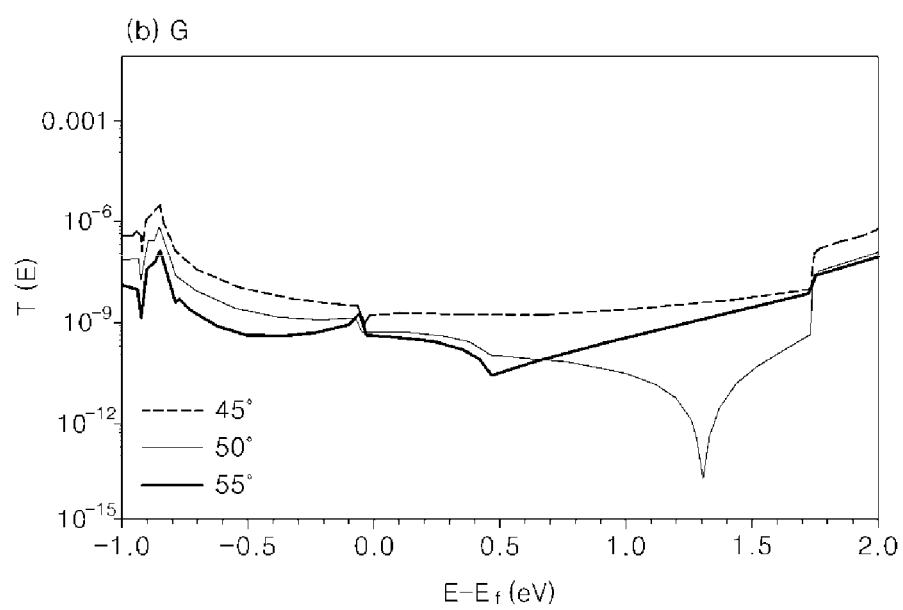

FIG. 11 shows zero bias transmission of DNA bases located in "cis" OH/H-gap for the rotation of (a) cytosine and (b) guanine in steps of 5°.

In addition to the phase conservation due to the base type and gap-edge termination, presence or number of oxygen in each DNA base plays an important role in transmission characteristics. Zero-bias transmission at Fermi-energy, T(Ef), varies two or three orders of magnitudes for C and G, which possess an oxygen. Also, a hierarchy of T(Ef) for C can be reversed depending on cis or trans gap-edge types. On the other hand, G keeps the order of magnitude of T(Ef) regardless of cis or trans.

(4) CONCLUSION

Quantum conductance for tunneling current through a DNA base varies depending on rotation angles with respect to the axis of the electrode, thereby rendering ambiguous current values, which cannot be implemented for base identification.

The present inventors investigated an origin of the ambiguity by using numerical analysis based on DFT-NEGF. In addition to the coupling strength, destructive quantum interference (DQI) and charge trapping might cause fluctuation in tunneling transmission, thereby generating broad range of tunneling currents.

Assuming realistic ketone-termination, mixture of "cis" and "trans," and externally driven rotation of base located in ZGNR electrode, A, when no dip is observed, could be distinguished. G could be identified whenever a couple of dips appeared at a couple of fixed angles. Due to the strong coupling induced angle-sensitivity, G shows fluctuation of transmission up to four orders of magnitudes, which can be used for its own identification. C and T, despite a fabrication issue, might be identified if the gap-edge termination can be controlled.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A device for determining a monomer molecule sequence of a polymer comprising:
   a pair of first electrodes that are formed of a first material and separated from each other by a gap;
   a pair of second electrodes that are separated from each other by a gap and formed of a material having electrical characteristics different from the electrical characteristics of the material of the pair of first electrodes;
   a pair of insulating materials between the pair of first electrodes and the pair of second electrodes, wherein the pair of insulating materials are separated from each other by a gap;
      wherein the gap separating the pair of first electrodes, the gap separating the pair of insulating materials, and the gap separating the pair of second electrodes are stacked in alignment to form a path through which a polymer can move;
   electrical signal detectors respectively connected to the pair of first electrodes and the pair of second electrodes;
   a polymer positioning unit for disposing the polymer in the path; and
   a polymer moving unit for rotating or left-right shifting or moving longitudinally along the path the polymer disposed in the path.

2. The device of claim 1, wherein the path has a cross-sectional length of about 10 nm or less.

3. The device of claim 1, wherein the pair of first electrodes include a carbonaceous electrode, a metal electrode, or any combination thereof, and the pair of second electrodes include a carbonaceous electrode, a metal electrode, or any combination thereof.

4. The device of claim 1, wherein the polymer positioning unit for disposing the polymer in the path is an electric field supply unit, a mechanical pressure supply unit, an optical tweezer, a magnetic tweezer, or any combination thereof.

5. The device of claim 1, wherein the polymer moving unit for rotating or left-right shifting the polymer disposed in the path is an optical tweezer, a magnetic tweezer, or any combination thereof.

6. The device of claim 1, wherein the polymer is DNA, RNA, or chimeric molecules thereof.

7. The device of claim 1, further comprising a signal processor that is electrically connected to the electrical signal detectors and comprises a storage medium storing a computer readable program that determines a monomer sequence of a polymer by using a method comprising: setting a first threshold value of an intensity of a signal received from the pair of first electrodes according to a monomer molecule of the polymer and identifying the type of the monomer from a signal having an intensity higher than the first threshold value; and setting a second threshold value of an intensity of a signal received from the pair of second electrodes according to the monomer molecule of the polymer and identifying the type of the monomer from a signal having an intensity higher than the second threshold value.

8. The device of claim 7, wherein the signal comprises an average of the signal with respect to a travel angle or distance according to the rotation or left-right shift of the polymer.

9. The device of claim 1, wherein the pair of first electrodes, the pair of second electrodes, or both are formed of a combination of different materials.

10. A method of determining a monomer molecule sequence of a polymer, the method comprising:
   disposing monomer molecules of a polymer in the path of the device of claim 1;
   detecting electrical signals respectively from the pair of first electrodes and the pair of second electrodes;
   setting a first threshold value of an intensity of a signal received from the pair of first electrodes according to a monomer molecule of the polymer and identifying the type of the monomer molecule from a signal having an intensity higher than the first threshold value, and setting a second threshold value of an intensity of a signal received from the pair of second electrodes according to the monomer molecule of the polymer and identifying the type of the monomer molecule from a signal having an intensity higher than the second threshold value; and determining the monomer molecule sequence of the polymer by combining the type of the monomer molecule identified by using the signal from the pair of first electrodes and the type of the monomer molecule identified by using the signal from the pair of second electrodes.

11. The method of claim 10, wherein the method comprises disposing multiple polymers in the path by disposing one polymer at a time.

12. The method of claim 10, wherein the polymer is DNA, RNA, or any combination thereof.

13. The method of claim 10, wherein the disposing of the polymer comprises holding the polymer in the path or passing the polymer through the path.

14. The method of claim 13, wherein the holding of the polymer is performed by holding the polymer at a predetermined position of the path by using an optical tweezer or magnetic tweezer.

15. The method of claim 14, wherein the detecting of the electrical signals comprises detecting a signal according to a travel angle or distance while rotating or left-right shifting the polymer, and calculating an average of the detected signal according to the travel angle or distance.

16. The method of claim 10, wherein the polymer comprises a nanoparticle or microparticle immobilized on at least one of a first end or second end of the polymer allowing the polymer to be moved by an optical tweezer or magnetic tweezer.

17. The method of claim 10, wherein the path comprises a first end to which the polymer is input and a second end from which the polymer is discharged, and the method further comprises immobilizing the polymer on a substrate movable with respect to the first end and the second end in the longitudinal direction along the path.

18. The method of claim 10, wherein the path has a cross-sectional length of about 10 nm or less.

19. The method of claim 10, wherein the pair of first electrodes includes a carbonaceous electrode, a metal electrode, or any combination thereof, and the pair of second electrodes includes a carbonaceous electrode, a metal electrode, or any combination thereof.

20. The method of claim 10, wherein the pair of first electrodes includes a graphene electrode, and the pair of second electrodes includes a gold electrode.

21. The method of claim 20, wherein the polymer is DNA, and the method further comprises setting a first threshold value of an intensity of a signal received from the pair of first electrodes according to a monomer molecule of a polymer as about 1 pA and identifying a base G or T from a signal having an intensity higher than the first threshold value, and setting a second threshold value of an intensity of a signal received from the pair of second electrodes according to a monomer molecule of a polymer as about 1 pA and identifying the type of the monomer molecule from a signal having an intensity higher than the second threshold value as a base A.

22. The method of claim 10, wherein the detecting of the electrical signals comprises detecting a signal according to a travel angle or distance while rotating or left-right shifting the polymer.

* * * * *